(12) United States Patent
Delcommenne

(10) Patent No.: US 12,044,680 B2
(45) Date of Patent: Jul. 23, 2024

(54) PEPTIDE EXCHANGE SYSTEM AND METHOD

(71) Applicant: MBL International Corp., Woburn, MA (US)

(72) Inventor: Marc Delcommenne, Chicago, IL (US)

(73) Assignee: MBL International Corp., Woburn, MA (US)

( * ) Notice: Subject to any disclaimer, the term of this patent is extended or adjusted under 35 U.S.C. 154(b) by 469 days.

(21) Appl. No.: 16/301,381

(22) PCT Filed: May 12, 2017

(86) PCT No.: PCT/US2017/032371
§ 371 (c)(1),
(2) Date: Nov. 13, 2018

(87) PCT Pub. No.: WO2017/197244
PCT Pub. Date: Nov. 16, 2017

(65) Prior Publication Data
US 2020/0326340 A1    Oct. 15, 2020

Related U.S. Application Data

(60) Provisional application No. 62/422,409, filed on Nov. 15, 2016, provisional application No. 62/336,189, filed on May 13, 2016.

(51) Int. Cl.
| | |
|---|---|
| *C07K 7/00* | (2006.01) |
| *C07K 14/74* | (2006.01) |
| *C07K 16/28* | (2006.01) |
| *C07K 16/44* | (2006.01) |
| *C07K 17/14* | (2006.01) |
| *G01N 33/566* | (2006.01) |
| *G01N 33/569* | (2006.01) |

(52) U.S. Cl.
CPC ..... *G01N 33/566* (2013.01); *C07K 14/70539* (2013.01); *C07K 17/14* (2013.01); *G01N 33/56977* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 5,635,363 A | 6/1997 | Altman et al. | |
| 2003/0059811 A1 | 3/2003 | Djaballah et al. | |
| 2005/0095655 A1 | 5/2005 | Montero-Julian et al. | |
| 2005/0100928 A1* | 5/2005 | Hedley | A61K 39/001191 435/325 |
| 2008/0044405 A1 | 2/2008 | DeDecker et al. | |
| 2010/0004161 A1 | 1/2010 | Apetoh et al. | |
| 2012/0214185 A1 | 8/2012 | Schwabe et al. | |
| 2014/0370524 A1 | 12/2014 | Springer et al. | |
| 2020/0326340 A1 | 10/2020 | Delcommenne | |

FOREIGN PATENT DOCUMENTS

| | | |
|---|---|---|
| CA | 2517097 A1 * | 9/2004 |
| CN | 1695060 A | 11/2005 |
| EP | 2952520 A1 | 12/2015 |
| JP | 2011/182702 A | 9/2011 |
| WO | WO-1992/007952 A1 | 5/1992 |
| WO | WO-1994/004171 A1 | 3/1994 |
| WO | WO-2002/103321 A2 | 12/2002 |
| WO | WO-2004/031362 A2 | 4/2004 |
| WO | WO-2005/010026 A2 | 2/2005 |
| WO | WO-2005/047902 A1 | 5/2005 |
| WO | WO-2006/013304 A1 | 2/2006 |

OTHER PUBLICATIONS

HLA Nomenclature (2015, 2 pages) (Year: 2015).*
Liu et al (MHC Complex: Interaction with Peptides. IN: eLS. John Wiley & Sons, Ltd: Chichester, DOI: 10.1002/9780470015902. a0000922.pub2, 2011, pp. 1-12) (Year: 2011).*
Wieczorek et al (Front. Immunol. 2017, vol. 8, article 292: 1-16) (Year: 2017).*
Eyers et al (Molec. Cell. Proteomics, 2011, 10: 10.1074/mcp.M110. 003384: 1-12) (Year: 2011).*
Ojcius et al (Eur. J. Immunol. 1993, 23: 1118-1124) (Year: 1993).*
Stone et al (PNAS, 2005, 102(10): 3744-3749) (Year: 2005).*
ThermoFisher Scientific (2023, The Molecular Probes Handbook, chapter 7, section 7.4, subsection "Anti-Dansyl Antibody") (Year: 2023).*
Saini et al (PNAS Sep. 17, 2013, 110(38): 15383-15388) (Year: 2013).*
Saini et al (PNAS, 2015, 112(1): 202-207) (Year: 2015).*
Hafstrand et al (PNAS, 2019, 116: 5055-5060) (Year: 2019).*
Anjanappa et al (Nature Comm., 2020 10.1038/s41467-020-14682-4: pp. 1-11) (Year: 2020).*
Jantz-Naeem and Springer (Curr. Opin. Immunol. 2021, 70: 82-89 (Year: 2021).*
McClusky et al (J. Immunol. 1988, 141: 1451-1455) (Year: 1988).*
Ostermeir et al (Mol. Immunol. 2015, 63: 312-319) (Year: 2015).*
Apetoh et al., "The interaction between HMGB1 and TLR4 dictates the outcome of anticancer chemotherapy and radiotherapy", Immunological Reviews, 220: 47-59, (2007).
Haan et al., "Enhanced Delivery of Exogenous Peptides into the Class I Antigen Processing and Presentation Pathway", Infection and Immunity, 70(6): 3249-3258 (2002).

(Continued)

*Primary Examiner* — Michael Szperka
*Assistant Examiner* — Marianne Dibrino
(74) *Attorney, Agent, or Firm* — Foley Hoag LLP; Hathaway P. Russell

(57) ABSTRACT

The methods and kits disclosed in the present disclosure allow quantified exchange of peptides into MHC proteins. These methods and kits allow MHC proteins with exchanged peptides to be used in further applications such as cell staining. The methods and kits may also be used to quantify peptides present in complex mixtures.

5 Claims, 16 Drawing Sheets

Specification includes a Sequence Listing.

(56) References Cited

OTHER PUBLICATIONS

Kim et al., "TNFR2-Deficient Memory CD8 T Cells Provide Superior Protection Against Tumor Cell Growth", The Journal of Immunology, 183: 6051-6057, (2009).
Truckenmiller et al., "Stress presents a problem for dendritic cells: Cortisone and the fate of MHC class I antigen processing presentation", 20(3): 210-218, (2006).
English Abstract for JP 2011/182702 A: 1 page (2011).
International Search Report and Written Opinion for International Application No. PCT/US17/32371 dated Sep. 6, 2017.
Extended European Search Report for EP Application No. EP 17796924 dated Dec. 5, 2019.
Altman et al., "MHC-peptide tetramers to visualize antigen-specific T cells." Curr Protoc Immunol. vol. 17, No. 17 (2003).
Luft et al., "Exogenous peptides presented by transporter associated with antigen processing (TAP)-deficient and TAP-competent cells: intracellular loading and kinetics of presentation." J. Immunol. vol. 167, pp. 2529-2537 (2001).
Rodenko et al., "Class I major histocompatibility complexes loaded by a periodate trigger." J Am Chem Soc , vol. 131, pp. 12305-12313. (2009).
Saini et al., "Dipeptides catalyze rapid peptide exchange on MHC class I molecules." Proc Natl Acad Sci , vol. 112, No. 1, pp. 202-207 (2015).
Toebes et al., Design and use of conditional MHC class I ligands. Nat Med, 12(2):246-251. (2006).

* cited by examiner

PEPTIDE EXCHANGE SYSTEM AND METHOD

REFERENCE TO RELATED APPLICATIONS

This application is a national stage filing under 35 U.S.C. § 371 of International Application No. PCT/US2017/032371, filed May 12, 2017, which claims the benefit of U.S. Provisional Application No. 62/336,189, filed May 13, 2016, and U.S. Provisional Application No. 62/422,409, filed Nov. 15, 2016. The contents of each of these applications is fully incorporated by reference herein.

SEQUENCE LISTING

The instant application contains a Sequence Listing which has been submitted electronically in ASCII format and is hereby incorporated by reference in its entirety. Said ASCII copy, created on Jun. 27, 2022, is named RBR-00601_SL.txt and is 16,246 bytes in size.

BACKGROUND OF THE INVENTION

During the immune response, antigen-presenting cells activate T lymphocytes through the interaction of MHC class I and II molecules with antigen-specific T cell receptors which in turn trigger CD4+ and CD8+ T lymphocyte proliferation. Detection of these antigen-specific CD4+ and CD8+ T cells is possible by use of MHC class II and class I tetramers, respectively, as described in U.S. Pat. No. 5,635,363 to Altman et al., which is fully incorporated by reference herein. MHC class I tetramers are formed by the binding of four biotinylated MHC-peptide monomers to fluorochrome-conjugated streptavidin. The T-cell receptor's ability to recognize the tetramer depends on both the MHC allele and the peptide sequence. The percentage of CD8+ T lymphocytes specific to a particular antigen/allele combination can be determined by staining leukocytes with fluorescent MHC class I tetramers in immunofluorescence multicolor assays followed by flow cytometry analysis. MHC class I monomers contain an MHC heavy chain, β2 microglobulin and the antigenic peptide. For most MHC class I molecules, successful in vitro folding of the MHC-peptide complex rests on the peptide binding to the heavy chain and requires that the peptide bind to the heavy chain with an affinity typically in the nanomolar range. The resulting tetramers are stable entities with peptides tightly bound to MHC proteins.

It is desirable to create MHC class I molecules containing peptides that may bind less tightly to the heavy chain during the folding process so that they can be easily replaced by peptides of interest or MHC binding molecules without affecting the integrity of the MHC complex. Peptide exchange or substitution by small molecules allows the creation of MHC-derived reagents that can be used to study different antigen-specific CD8+T cell populations. Some techniques are known for peptide exchange in MHC proteins, for instance as described in Springer, et al., U.S. Patent Publication No. 2014/0370524, the contents of which are fully incorporated by reference herein. However, techniques are needed for quantifying peptide exchange. This is necessary, e.g., for the tetramers to be used in flow cytometry staining.

SUMMARY OF THE INVENTION

In one aspect, the present disclosure provides methods to perform peptide exchange on MHC proteins, such as quantified peptide exchange. The MHC proteins may be class I or class II molecules, and they may be exchanged in any multimeric state, such as monomers, tetramers, octamers, or dodecamers.

In another aspect, the present disclosure provides MHC class I tetramers with high peptide exchangeability, and methods for producing them.

In another aspect, the present disclosure provides MHC class I tetramers with exchanged peptides.

In another aspect, the present disclosure provides compositions and kits for performing the methods disclosed herein.

BRIEF DESCRIPTION OF THE DRAWINGS

FIG. 1A shows the selection of single beads and exclusion of doublets and larger clumps. FIG. 1B shows setting of PMT voltages and gains based on unused beads to have mean fluorescence intensities (MFI) in the first log decade (about 0.2-0.3. FIG. 1C shows compensation on the FL1 channel to eliminate fluorochrome interference in the FITC channel. FIG. 1D shows the calibration level for 0% tagged peptide, i.e. 100% peptide exchange. FIG. 1E shows the calibration level for 100% tagged peptide, i.e. 0% peptide exchange. FIG. 1F shows exemplary data for a sample exchange.

FIG. 6 shows peptide exchange results with exiting peptides MTYK(DNP)FPVT (SEQ ID NO: 1) and YTVK(DNP)FALV (SEQ ID NO: 2), and various entering peptides.

FIG. 7 shows the results of peptide exchange experiments with exiting peptides ILKEKK(DNP)VHGV (SEQ ID NO: 3) and ILKEK(DNP)VHGV (SEQ ID NO: 4), and entering peptide YLLEFTPPV (SEQ ID NO: 5) at various concentrations.

DETAILED DESCRIPTION OF THE INVENTION

Figure 1A:
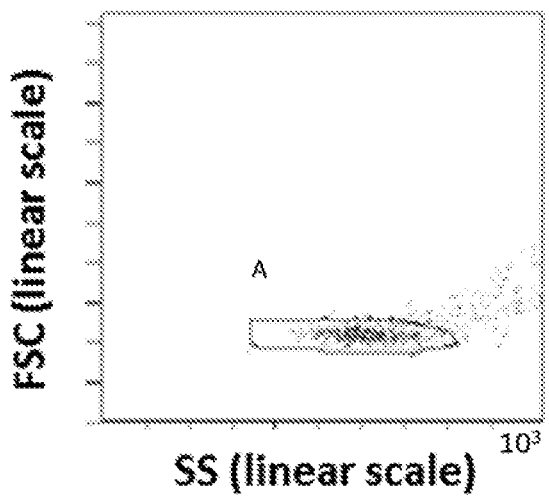
FIGS. 1A-1F illustrate an exemplary protocol for conducting the methods described herein.

In some aspects, the present disclosure provides a method of performing peptide exchange on an MHC molecule, comprising:

providing the MHC molecule bound to a first peptide; and contacting the MHC molecule bound to the first peptide with a second binding partner, optionally in combination with a third binding partner, optionally in the presence of a peptide exchange factor, wherein the contacting step generates an MHC molecule bound to the second binding partner and optionally the third binding partner.

In some embodiments, the peptide exchange is performed on a quantity of MHC molecules. According to these embodiments, the method comprises:

providing a first quantity of MHC molecules bound to a first peptide; and adding to the MHC molecules bound to the first peptide, optionally a peptide exchange factor, and a second quantity of a second binding partner, optionally in combination with a third binding partner, whereby a resulting mixture is formed comprising MHC molecules bound to the first peptide or MHC molecules bound to the second binding partner and optionally the third binding partner, and unbound first peptide or unbound second binding partner and optionally third binding partner.

In some embodiments, the second binding partner is a peptide. In some embodiments, the second binding partner is a non-peptide ligand for MHC proteins. For example, as described in U.S. Patent Pub. No. US 2008/0044405, certain noble metal ion-containing compounds can form a complex with class II MHC proteins and interfere with their peptide-binding abilities.

In some embodiments, a second and third binding partner are provided. According to these embodiments, the second and third binding partner bind together to the MHC. For example, abacavir is believed to bind to MHC allele HLA-B*57:01, which alters the binding groove such that abacavir-bound HLA-B*57:01 can bind to different peptides than non-abacavir-bound HLA-B*57:01.

In some aspects, the present disclosure provides a method of performing peptide exchange on an MHC molecule, comprising:

providing the MHC molecule bound to a first peptide; and contacting the MHC molecule bound to the first peptide with a second peptide, optionally in the presence of a peptide exchange factor, wherein the contacting step generates an MHC molecule bound to the second peptide.

In some embodiments, the peptide exchange is performed on a quantity of MHC molecules. According to these embodiments, the method comprises:

providing a first quantity of MHC molecules bound to a first peptide; and adding to the MHC molecules bound to the first peptide, optionally a peptide exchange factor, and a second quantity of a second peptide, whereby a resulting mixture is formed comprising MHC molecules bound to the first peptide or MHC molecules bound to the second peptide, and unbound first peptide or unbound second peptide.

In some embodiments of the above, the MHC molecule is an MHC class I molecule. In some embodiments, the MHC molecule is an MHC class II molecule.

In some aspects, the present disclosure provides methods of performing peptide exchange on an MHC class I molecule, comprising:

providing the MHC class I molecule bound to a first (i.e., an exiting) peptide; and contacting the MHC class I molecule bound to a first peptide with a second (i.e., an entering) peptide, optionally in the presence of a peptide exchange factor, wherein the contacting step generates an MHC class I molecule bound to the second peptide.

In some embodiments, the peptide exchange is performed on a quantity of MHC class I molecules. According to these embodiments, the method comprises:

providing a first quantity of MHC class I molecules bound to a first peptide; and adding to the MHC class I molecules bound to the first peptide, optionally a peptide exchange factor and a second quantity of a second peptide, whereby a resulting mixture is formed comprising MHC class I molecules bound to the first peptide or MHC class I molecules bound to the second peptide, and unbound first peptide or unbound second peptide.

In some aspects, the present disclosure provides methods of performing peptide exchange on an MHC class II molecule, comprising:

providing the MHC class II molecule bound to a first (i.e., an exiting) peptide; and contacting the MHC class II molecule bound to a first peptide with a second (i.e., an entering) peptide, optionally in the presence of a peptide exchange factor, wherein the contacting step generates an MHC class II molecule bound to the second peptide.

In some embodiments, the peptide exchange is performed on a quantity of MHC class II molecules. According to these embodiments, the method comprises:

providing a first quantity of MHC class II molecules bound to a first peptide; and adding to the MHC class II molecules bound to the first peptide, optionally a peptide exchange factor and a second quantity of a second peptide, whereby a resulting mixture is formed comprising MHC class II molecules bound to the first peptide or MHC class II molecules bound to the second peptide, and unbound first peptide or unbound second peptide.

In some embodiments, the second binding partner (such as the second peptide) is added in excess over the first peptide. In some embodiments, the exchange is complete, such that the resulting mixture does not contain MHC molecules, such as MHC class I molecules bound to the first peptide. In some embodiments, the exchange is substantially complete and the resulting mixture comprises MHC molecules, such as MHC class I molecules bound to the first peptide, MHC molecules, such as MHC class I molecules bound to the second binding partner (such as the second peptide), unbound first peptide, and unbound second binding partner (such as the second peptide). In some embodiments, the exchange is 99% complete, i.e., in the resulting mixture, 99% of the MHC class I molecules are bound to the second binding partner (such as the second peptide). In some embodiments, the exchange is 95% complete, 90% complete, 85% complete, 80% complete, 75% complete, 70% complete, 65% complete, 60% complete, 55% complete, 50% complete, 40% complete, 30% complete, 20% complete, or 10% complete.

In some embodiments, the first peptide is labeled with a first label. The label may be any characteristic of the peptide that makes it distinguishable or detectable by methods known in the art. For instance, the label may be an amino acid sequence recognizable by an antibody, e.g. an epitope tag, or a fluorophore. Exemplary labels and detection methods are disclosed herein. In some embodiments, the first label is selected from an epitope tag, a fluorescent tag, a quencher, a radiolabel, or an amino acid modification such as phosphorylation, glycosylation, or sulfation. In some embodiments, the first label is an epitope tag, such that the first peptide displays a first epitope tag. In some embodiments, two different labels are conjugated to two different regions of the exiting peptide. According to these embodiments, quantitation can be performed by the methods disclosed herein on two resulting fragments of cleavable peptides after cleavage (where cleavage can be performed, e.g., by UV irradiation or by periodate).

In some embodiments, the second binding partner (such as the second peptide) is labeled with a second label, which may be different from the first label. In some embodiments, the second label is selected from an epitope tag, a fluorescent tag, a quencher, a radiolabel, or an amino acid modification such as phosphorylation, glycosylation, or sulfation. In some embodiments, the second label is an epitope tag, such that the first peptide displays a first epitope tag. In some embodiments, the second binding partner (such as the second peptide) is not labeled.

In some embodiments, the method further comprises quantifying the completeness of the peptide exchange. In some embodiments, this comprises determining at least one of the following quantities: the amount of MHC molecules bound to the first peptide, the amount of MHC molecules bound to the second binding partner (such as the second peptide), the amount of unbound first peptide, or the amount of unbound second binding partner (such as the second peptide). In some embodiments, the method further comprises determining the amount of unbound first peptide and comparing the amount of unbound first peptide to the amount of the first quantity of MHC molecules, such as MHC class I molecules, bound to a first peptide. In some embodiments, the measuring step is accomplished by performing an immunoassay. In some embodiments, the immunoassay is a sandwich immunoassay.

In some embodiments, performing a sandwich immunoassay comprises:
  providing a support, such as beads or microplate wells, conjugated to a first antibody;
  binding the first antibody to both the MHC molecules bound to the first peptide and the MHC molecules bound to the second binding partner (such as the second peptide);
  providing a second antibody capable of binding the first peptide;
  binding the second antibody to the MHC molecules bound to the first peptide, whereby the second antibody is bound to the support, e.g. beads or microplate wells;
  determining the amount of the second antibody that is bound to the support, e.g. beads or microplate wells.

Figure 3A:
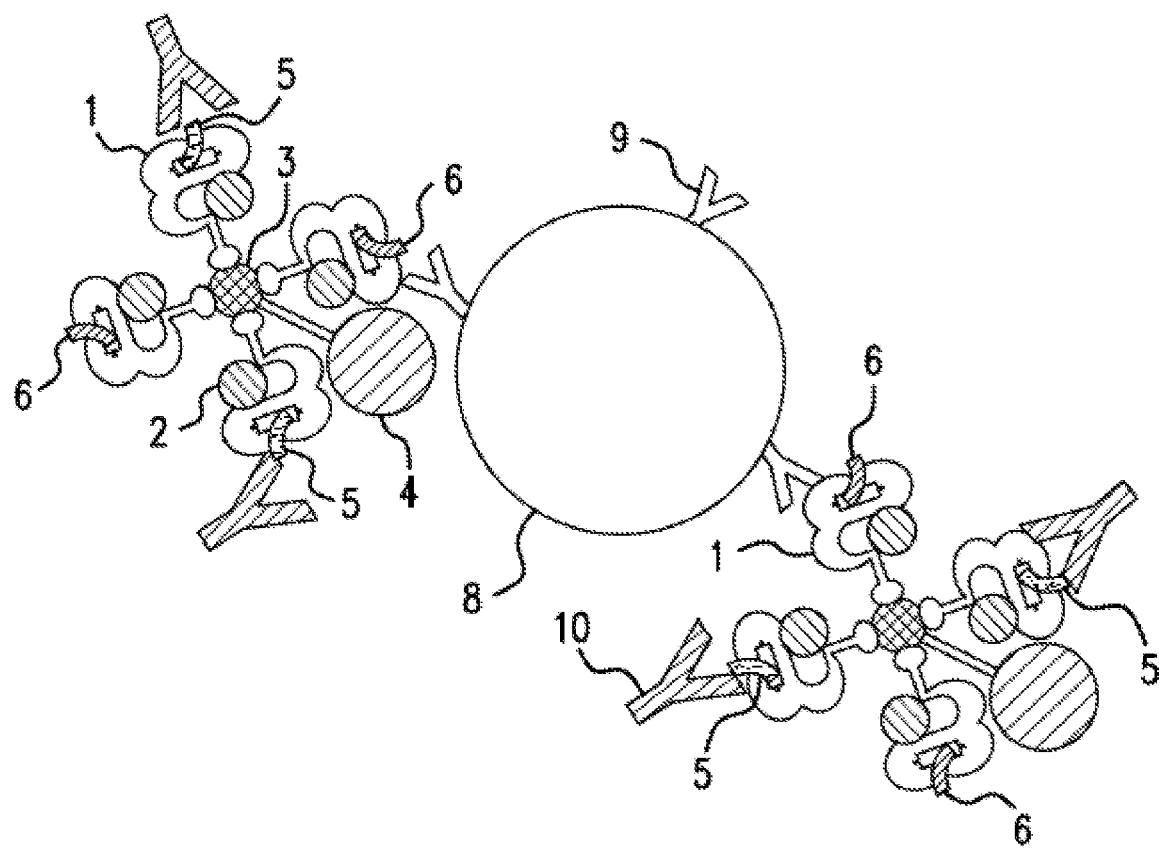
FIGS. 3A and 3B are schematic depictions of the sandwich immunoassay described herein.
Figure 3B:
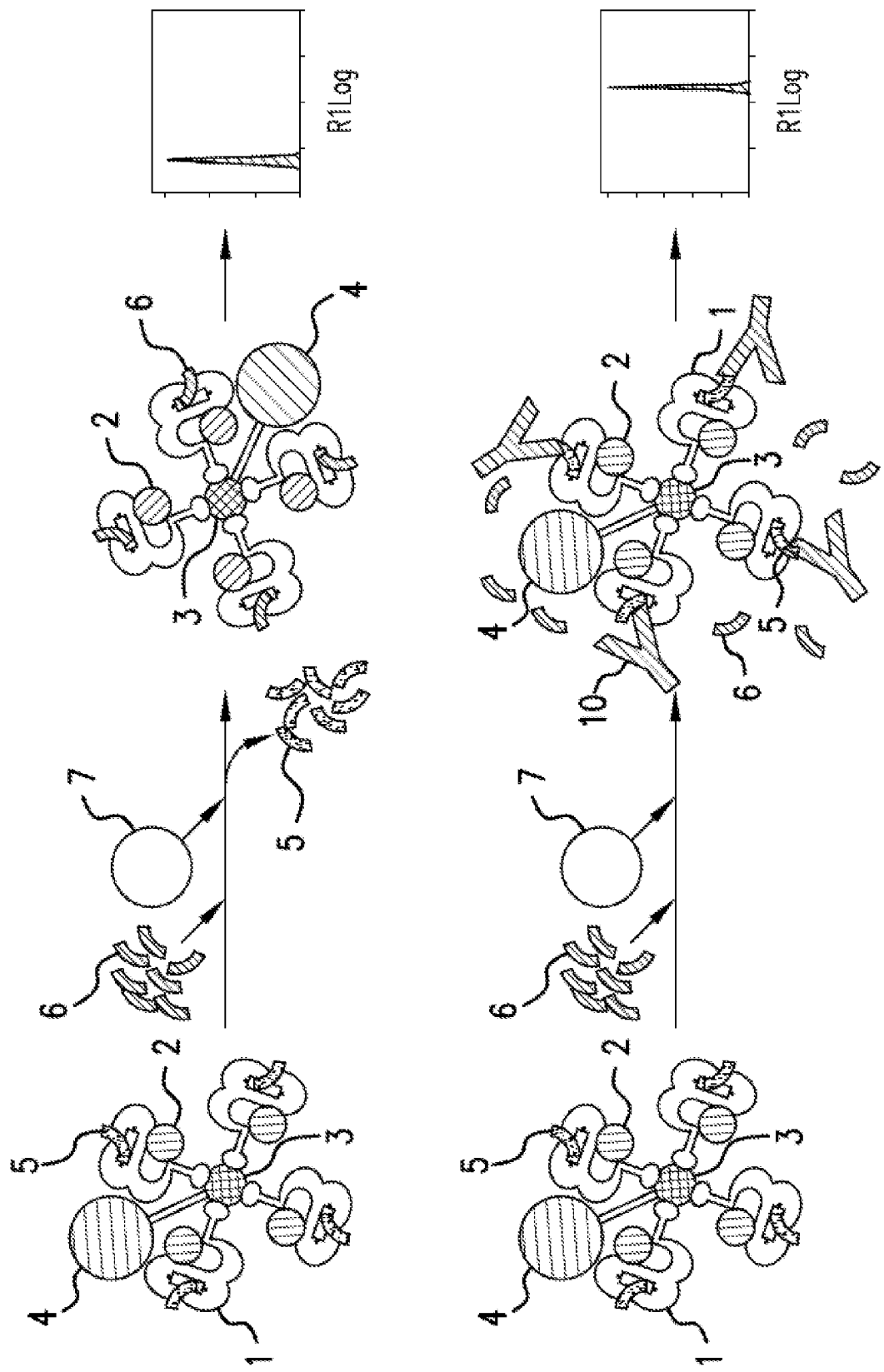

This general procedure is depicted in FIGS. 3A and 3B. In some embodiments, the support comprises beads. In some such embodiments, performing the sandwich immunoassay comprises pelleting the beads using a magnet, be centrifugation, or by suction. In some embodiments, the support comprises microplate wells.

In some embodiments, the measuring step comprises performing a fluorescence measurement.

In some embodiments, the first antibody is an anti-MHC or anti-streptavidin antibody.

The second antibody used in the sandwich immunoassay may be selected according to the tag on the first peptide. For example, the first peptide may be labeled with DNP and the second antibody may be an anti-DNP antibody. Alternatively, the tags and antibodies may be as described herein. In alternative embodiments, the second antibody may be replaced by a ligand or a lectin matched to a tag on the first peptide, as described herein.

The second antibody may be labeled as described herein, for example with a fluorophore or a radiolabel.

In some embodiments, the method further comprises conducting a control peptide exchange.

In some aspects, the present disclosure provides a kit for peptide exchange comprising an MHC class I molecule bound to a first peptide and a peptide exchange factor.

In some embodiments, the first peptide is labeled with a first label. The label may be any characteristic of the peptide that makes it distinguishable or detectable by methods known in the art. For instance, the label may be an amino acid sequence recognizable by an antibody, e.g. an epitope tag, or a fluorophore. Exemplary labels and detection methods are disclosed herein. In some embodiments, the first label is selected from an epitope tag, a fluorescent tag, a quencher, or a radiolabel. In some embodiments, the first label is an epitope tag, such that the first peptide displays a first epitope tag.

In some embodiments, the first peptide displays a first epitope tag and the kit further comprises an anti-first epitope tag antibody. In some embodiments, the first peptide displays a first epitope tag and the kit further comprises a capture system comprising anti-first tag antibodies.

In some embodiments, the kit further comprises a reference peptide.

In some embodiments, the MHC protein is an MHC class I molecule. In some embodiments, the MHC class I molecule is a monomer. In some embodiments, the MHC class I molecule is a component of a multimer. In some embodiments, the multimer comprises 4 MHC class I molecules. In some embodiments, the multimer comprises 6 MHC class I molecules. In some embodiments, the multimer comprises 12 MHC class I molecules.

In some embodiments, the MHC class I molecule is HLA-A*02:01.

In some embodiments, the MHC protein is an MHC class II molecule. In some embodiments, the MHC class II molecule is a monomer. In some embodiments, the MHC class II molecule is a component of a multimer. In some embodiments, the multimer comprises 4 MHC class I molecules. In some embodiments, the multimer comprises 6 MHC class II molecules. In some embodiments, the multimer comprises 12 MHC class II molecules.

In some embodiments, the MHC class II molecule is HLA-DR4.

In some embodiments, a peptide exchange factor is used. The peptide exchange factor may be any known in the art. In some embodiments, the peptide exchange factor is peptide exchange factor 1, glycyl-methionine, glycyl-cyclohexylalanine, glycyl-leucine, glycyl-arginine, glycyl-lysine, glycyl-(tert)-butylalanine, or glycyl-homoleucine.

In some embodiments, the first peptide is ILKEKK(DNP)VHGV (SEQ ID NO: 3), SIINK(DNP)EKL (SEQ ID NO: 7), MTYK(DNP)FPVT (SEQ ID NO: 1), or YTVK(DNP)FALV (SEQ ID NO: 2). In some embodiments, the first peptide is a functional homologue thereof having at least 75% identity, at least 80% identity, or at least 90% identity with ILKEKK(DNP)VHGV (SEQ ID NO: 3), SIINK(DNP)EKL (SEQ ID NO: 7), MTYK(DNP)FPVT (SEQ ID NO: 1), or YTVK(DNP)FALV (SEQ ID NO: 2).

In some embodiments, the second peptide is ILKEKKVHGV (SEQ ID NO: 8), SIINKEKL (SEQ ID NO: 9), MTYKFPVT (SEQ ID NO: 10), YTVKFALV (SEQ ID NO: 11), ELAGIGILTV (SEQ ID NO: 12), ILKEPVHGV (SEQ ID NO: 13), AAGIGILTV (SEQ ID NO: 14), YLLEFTPPV (SEQ ID NO: 5), or KAFSPEVIPMF (SEQ ID NO: 15). In some embodiments, the first peptide is a functional homologue thereof having at least 75% identity, at least 80% identity, or at least 90% identity with ILKEKKVHGV (SEQ ID NO: 8), SIINKEKL (SEQ ID NO: 9), MTYKFPVT (SEQ ID NO: 10), YTVKFALV (SEQ ID NO: 11), ELAGIGILTV (SEQ ID NO: 12), ILKEPVHGV (SEQ ID NO: 13), AAGIGILTV (SEQ ID NO: 14), YLLEFTPPV (SEQ ID NO: 5), or KAFSPEVIPMF (SEQ ID NO: 15).

MHC Proteins

The MHC proteins provided and used in the methods of the present disclosure may be any suitable MHC molecules known in the art where it is desirable to exchange the peptide that the MHC protein originally contained with another peptide. Generally, they have the formula $(\alpha\text{-}\beta\text{-}P)_n$, where n is at least 2, for example between 2-10, e.g. 4. $\alpha$ is an a chain of a class I or class II MHC protein. $\beta$ is a $\beta$ chain, herein defined as the $\beta$ chain of a class II MHC protein or $\beta_2$ microglobulin for a MHC class I protein. P is a peptide antigen.

The MHC proteins may be from any mammalian or avian species, e.g. primate sp., particularly humans; rodents, including mice, rats and hamsters; rabbits; equines, bovines, canines, felines; etc. For instance, the MHC protein may be derived the human HLA proteins or the murine H-2 proteins. HLA proteins include the class II subunits HLA-DP$\alpha$, HLA-DP$\beta$, HLA-DQ$\alpha$, HLA-DQ$\beta$, HLA-DR$\alpha$ and HLA-DR$\beta$, and the class I proteins HLA-A, HLA-B, HLA-C, and $\beta$2-microglobulin. H-2 proteins include the class I subunits H-2K, H-2D, H-2L, and the class II subunits I-A$\alpha$, I-A$\beta$, I-E$\alpha$ and I-E$\beta$, and $\beta$2-microglobulin. Sequences of some representative MHC proteins may be found in Kabat et al. Sequences of Proteins of Immunological Interest, NIH Publication No. 91-3242, pp 724-815. MHC protein subunits suitable for use in the present invention are a soluble form of the normally membrane-bound protein, which is prepared as known in the art, for instance by deletion of the transmembrane domain and the cytoplasmic domain.

For class I proteins, the soluble form will include the $\alpha$1, $\alpha$2 and $\alpha$3 domain. Soluble class II subunits will include the $\alpha$1 and $\alpha$2 domains for the a subunit, and the $\beta$1 and $\beta$2 domains for the $\beta$ subunit.

The $\alpha$ and $\beta$ subunits may be separately produced and allowed to associate in vitro to form a stable heteroduplex complex, or both of the subunits may be expressed in a single cell. Methods for producing MHC subunits are known in the art.

To prepare the MHC-peptide complex, the subunits may be combined with an antigenic peptide and allowed to fold in vitro to form a stable heterodimer complex with intrachain disulfide bonded domains. The peptide may be included in the initial folding reaction, or may be added to the empty heterodimer in a later step. In the methods of the present invention, this will be the exiting peptide. Conditions that permit folding and association of the subunits and peptide are known in the art. As one example, roughly equimolar amounts of solubilized $\alpha$ and $\beta$ subunits may be mixed in a solution of urea. Refolding is initiated by dilution or dialysis into a buffered solution without urea. Peptides may be loaded into empty class II heterodimers at about pH 5 to 5.5 for about 1 to 3 days, followed by neutralization, concentration and buffer exchange. However, the specific folding conditions are not critical for the practice of the invention.

The monomeric complex ($\alpha$-$\beta$-P) (herein monomer) may be multimerized. The resulting multimer will be stable over long periods of time. Preferably, the multimer may be formed by binding the monomers to a multivalent entity through specific attachment sites on the $\alpha$ or $\beta$ subunit, as known in the art (e.g., as described in U.S. Pat. No. 5,635,363). The MHC proteins, in either their monomeric or multimeric forms, may also be conjugated to beads or any other support.

Frequently, the multimeric complex will be labeled, so as to be directly detectable when used in immunostaining or other methods known in the art, or will be used in conjunction with secondary labeled immunoreagents which will specifically bind the complex, as known in the art and as described herein. For example, the label may be a fluorophore, such as fluorescein isothiocyanate (FITC), rhodamine, Texas Red, phycoerythrin (PE), allophycocyanin (APC), Brilliant Violet™ 421, Brilliant UV™ 395, Brilliant Violet™ 480, Brilliant Violet™ 421 (BV421), Brilliant Blue™ 515, APC-R700, or APC-Fire750. In some embodiments, the multimeric complex is labeled by a moiety that is capable of specifically binding another moiety. For instance, the label may be biotin, streptavidin, an oligonucleotide, or a ligand. Other labels of interest may include dyes, enzymes, chemiluminescers, particles, radioisotopes, or other directly or indirectly detectable agent.

The methods disclosed herein may be used to perform peptide exchange on any suitable MHC protein. Exemplary MHC proteins of use in the methods and with the peptides disclosed here include H-2 Kb monomer, HLA-A*02:01 monomer, HLA-A*24:02 monomer, HLA-A*02:01 tetramer, HLA-A*24:02 tetramer, and H-2 Kb tetramer. However, any MHC allele may be used in the methods herein upon selection of an appropriate exiting peptide, according for example to known techniques for predicting the affinity of a peptide to an MHC allele.

Labels for Quantification of Peptide Exchange

According to some embodiments of the methods disclosed herein, the exiting peptide (i.e., the peptide that is to be exchanged) is labeled such that the proportion of the exiting peptide that remains bound to the MHC proteins may be quantified, for example by a sandwich immunoassay.

Labels particularly adapted to quantification of the exchange are those that do not render the peptide unable to bind to the MHC protein, and which are capable of specifically binding to a detecting moiety. Exemplary specific binding pairs include biotin or variants thereof with streptavidin or variants thereof, tags with their complementary antibodies, ligands, or lectins, haptens with the proteins they bind to, or oligonucleotide sequences with their complement.

Thus, in some embodiments an exiting peptide may be labeled with a tag, i.e. a moiety recognizable by an antibody, a lectin, or a specific ligand. Exemplary tags include dinitrophenol (DNP), sialic acid, nitrosyl, sulfated saccharides, O-glycosylated amino acids, N-glycosylated amino acids, phosphoserine, phosphothreonine, and phosphotyrosine.

In some embodiments, an exiting peptide may be labeled with a biotin moiety or a known biotin variant for binding to streptavidin or a streptavidin variant. Exemplary biotin variants are 2-iminobiotin, carboxybiotin, biocytin, or iminobiocytin.

An exiting peptide labeled as described will bind with a binding partner specific to the label on the exiting peptide. The binding partner may be labeled with a moiety capable of direct detection, such as a fluorescent moiety or a radio-label, or a moiety capable of indirect detection, for instance an enzyme label such as horseradish peroxidase (HRP) or alkaline phosphatase. Then the MHC proteins that are unexchanged—i.e., those that retain the exiting peptide—may be detected, for instance, by a sandwich assay in which capture beads or any other suitable support conjugated with anti-MHC protein antibodies are used to capture the MHC protein, and the binding partner is used to identify those MHC proteins that are still bound to the exiting peptide. The result of the sandwich assay can be seen in FIG. 3A: MHC proteins are formed by the combination of the a subunit (1) and the β subunit (2). The MHC proteins are tetramerized by attachment to a streptavidin (3). The tetrameric MHC complex is labeled (e.g. with a fluorophore) (4). Bound to each MHC protein in the complex is either the exiting peptide (5) or the entering peptide (6). The MHC tetramers are bound to a bead or any other suitable support (8) through an MHC antibody (9). Where the exiting peptide (5) is still associated with the MHC protein, a labeled anti-tag antibody (10) will bind. Where the entering peptide (6) has replaced the exiting peptide, the labeled anti-tag antibody will not bind. As seen in 3B, a high level of exchange leads to no exiting peptide remaining associated with the MHC proteins (top), and accordingly the anti-tag antibody does not bind and a low fluorescence signal is measured. A low level of exchange leads to high retention of the exiting peptide (bottom), so a large amount of the anti-tag antibody binds, and a high fluorescence signal is observed.

In embodiments where the binding partner is labeled with an enzyme label (such as a HRP), instead of measuring fluorescence levels, a substrate of the enzyme (such as tetramethylbenzidine (TMB), 3,3'-diaminobenzidine (DAB), or 2,2'-azino-bis(3-ethylbenzothiazoline-6-sulphonic acid) (ABTS)) may be added to develop a detectable color. A high level of exchange leads to no exiting peptide remaining associated with the MHC proteins, and accordingly the anti-tag antibody does not bind, no enzyme is present, and no color develops. A low level of exchange leads to high retention of the exiting peptide, so a large amount of the anti-tag antibody binds, a large amount of the enzyme is present, so a color develops.

Exemplary fluorescent moieties that may be used to label the binding partner (e.g., that may be used to label the antibody) include 7-amino-4-methyl-coumarin (AMC), 5-((2-aminoethyl)amino)naphthalene-1-sulfonic acid (EDANS), FITC, FAM, 7-nitrobenz-2-oxa-1,3-diazole (NBD), Rhodamine B, TAMRA, or any other suitable fluorescent moiety.

Exemplary radiolabels that may be used to label the binding partner (e.g., that may be used to label the antibody) include $^{32}P$, $^{35}S$ methionine, and $^{125}I$. Methods for using such radiolabels in connection with antibodies, lectins, or ligands are known in the art.

Peptide Exchange Factors

Any suitable peptide exchange factor may be used in the methods provided herein. Exemplary peptide exchange factors include glycyl-methionine, glycyl-cyclohexylalanine, glycyl-leucine, glycyl-arginine, glycyl-lysine, glycyl-(tert)-butylalanine, glycyl-homoleucine.

Exiting Peptides

Those of skill in the art will be able to create exiting peptides in addition to those described herein, including exiting peptides with various labels and various sequences that are adapted to bind at a suitable strength to any one of the many known MHC alleles. Such exiting peptides may be designed by known techniques, such as by available tools to predict the affinity of a particular peptide to a particular MHC allele. They may optionally be labeled as disclosed herein. Exemplary exiting peptides disclosed herein include ILKEKK(DNP)VHGV (SEQ ID NO: 3), ILKEK(DNP)VHGV (SEQ ID NO: 4), SIINK(DNP)EKL (SEQ ID NO: 7), MTYK(DNP)FPVT (SEQ ID NO: 1), TFQRK(DNP)PAAF (SEQ ID NO: 16), or YTVK(DNP)FALV (SEQ ID NO: 2). Other exemplary exiting peptides are those having at least 75%, 80%, 85%, 90%, or 95% sequence identity with the foregoing.

Entering Peptides

Those of skill in the art will be able to create entering peptides in addition to those described herein, including entering peptides with various labels and various sequences that are adapted to bind at a suitable strength to any one of the many known MHC alleles, such as a binding strength that is greater or comparable to the exiting peptide being used. Such entering peptides may be designed by known techniques, such as by available tools to predict the affinity of a particular peptide to a particular MHC allele. They may optionally be labeled as disclosed herein. Exemplary entering peptides disclosed herein include ILKEKKVHGV (SEQ ID NO: 8), ILKEKVHGV (SEQ ID NO: 17), SIINKEKL (SEQ ID NO: 9), MTYKFPVT (SEQ ID NO: 10), YTVKFALV (SEQ ID NO: 11), ELAGIGILTV (SEQ ID NO: 12), ILKEPVHGV (SEQ ID NO: 13), AAGIGILTV (SEQ ID NO: 14), YLLEFTPPV (SEQ ID NO: 5), KAFSPEVIPMF (SEQ ID NO: 15), AMAPRTLLL (SEQ ID NO: 18), ATDALMTGY (SEQ ID NO: 19), EVDPIGHLY (SEQ ID NO: 20), FLSELTQQL (SEQ ID NO: 21), FMYSDFHFI (SEQ ID NO: 22), GLADQLIHL (SEQ ID NO: 23), GLAVVTHGL (SEQ ID NO: 24), GYSLKLSKL (SEQ ID NO: 25), IMDQVPFSV (SEQ ID NO: 26), IYSTVASSL (SEQ ID NO: 27), LNMADKKET (SEQ ID NO: 28), RAHYNIVTF (SEQ ID NO: 29), RVRAYTYSK (SEQ ID NO: 30), RYMRWTYRF (SEQ ID NO: 31), SLYNTVATL (SEQ ID NO: 32), FLYDDNQRV (SEQ ID NO: 33), GLADQLIHL (SEQ ID NO: 23), AVLDGLLSL (SEQ ID NO: 34), GLAVVTHGL (SEQ ID NO: 24), WMHKVPASL (SEQ ID NO: 35), CINGVCWTV (SEQ ID NO: 36), WMHHNMDLI (SEQ ID NO: 37), SLPPPGTRV (SEQ ID NO: 38), LTLGEFLKL (SEQ ID NO: 39), IMQLMPFGC (SEQ ID NO: 40), IMQIMPYGC (SEQ ID NO: 41), RIKDFLRNL (SEQ ID NO: 42), ALLAVGATK (SEQ ID NO: 43), CSLWNGPHL (SEQ ID NO: 44), EYILSLEEL (SEQ ID NO: 45), ALALEVGEL (SEQ ID NO: 46), SYVPSAEQI (SEQ ID NO: 47), ATVQGQNLK (SEQ ID NO: 48), or IRLRPGGKK (SEQ ID NO: 49). Other exemplary entering peptides are those having at least 75%, 80%, 85%, 90%, or 95% sequence identity with the foregoing.

Media for Exchange

The methods described herein may be performed in any suitable medium.

In some embodiments, the reaction mixture contains the reagents in a buffered solution. Thus, the reaction mixture may consist essentially of an MHC molecule bound to a first (exiting) peptide, a second (entering) peptide, and a peptide exchange factor. According to these embodiments, the MHC molecule, the first peptide, the second binding partner (such as the second peptide), and the peptide exchange factor may all be as described herein.

In some embodiments, the reaction mixture contains the reagents in a solution, and the solution may comprise other species, such as peptides other than the first and second peptides, lipids, polynucleotides, or other biological or non-biological species. In certain embodiments, the solution may comprise bodily fluids, tissue extracts from normal or abnormal tissues, cell extracts from normal or abnormal tissues, cell extracts from tumors, or cell extracts from other pathologies. In certain embodiments, the solution may comprise extracts or lysates of microorganisms such as viruses, bacteria, parasites, or yeast. In certain embodiments, the solution may comprise environmental water, air and soil samples, or extracts thereof. In certain embodiments, the solution may comprise synthetic mixtures, such as protein hydrolysates, perfusions, vaccines, or synthetic tissue culture media. According to these embodiments, the MHC molecule, the first peptide, the second binding partner (such as the second peptide), and the peptide exchange factor may all be as described herein.

Kits

In some aspects, the present disclosure provides kits for peptide exchange, such as quantified peptide exchange. The kits may comprise several modules, which may include an MHC module, a peptide detection module, an exchange factor module, and/or a reference peptide module. The components of the kit may be selected such that the user of the kit is able to prepare the remainder of the necessary components for conducting the methods disclosed herein.

The MHC module will generally include the MHC protein for exchange (in monomeric or multimeric form), for instance including the exiting peptide lyophilized or in solution. The solution is advantageously buffered, and may also contain other components to stabilize the solution. For instance, the solution may contain protein stabilizers and/or sodium azide. The peptide associated with the MHC protein is generally labeled as described herein. The sequence of the peptide is selected to provide stability of the kit MHC protein and exchangeability against a peptide of interest.

The peptide detection module will generally contain any suitable peptide detection system that is matched with the labeled exchangeable peptide provided in the MHC module. For instance, if the detection system contemplates a sandwich magnetic bead immunoassay, then the detection module may contain a vial comprising magnetic beads coupled with MHC capture antibody, and a vial comprising a fluorescently-tagged antibody that is reactive against the exiting peptide (in the case of tagged peptides).

The exchange factor module will generally contain a peptide exchange factor, lyophilized or in solution. The solution is advantageously buffered, and may also contain other components to stabilize the solution. For instance, the solution may contain protein stabilizers and/or sodium azide.

Definitions

The articles "a" and "an" are used herein to refer to one or to more than one (i.e., to at least one) of the grammatical object of the article. By way of example, "an element" means one element or more than one element.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof; amino acid analogs having variant side chains; and all stereoisomers of any of any of the foregoing.

The phrase "derived from" when used concerning a rearranged variable region gene "derived from" an unrearranged variable region and/or unrearranged variable region gene segments refers to the ability to trace the sequence of the rearranged variable region gene back to a set of unrearranged variable region gene segments that were rearranged to form a gene that expresses the variable domain (accounting for, where applicable, splice differences and somatic mutations). For example, a rearranged variable region gene that has undergone somatic mutation is still derived from the unrearranged variable region gene segments. In some embodiments, where the endogenous locus is replaced with a universal light chain or heavy chain locus, the term "derived from" indicates the ability to trace origin of the sequence to said rearranged locus even though the sequence may have undergone somatic mutations.

EXAMPLES

The invention now being generally described, it will be more readily understood by reference to the following examples which are included merely for purposes of illustration of certain aspects and embodiments of the present invention, and are not intended to limit the invention.

Example 1: Exemplary Protocol for Measurement of Peptide Replacement

Reagents: The following stock solutions are prepared or provided:

Tetramer (e.g. HLA-A*02:01) with exiting peptide in a buffered 50 µg/mL (measured by monomer content) solution with added protein stabilizers and ≤0.09% sodium azide.

Peptide exchange factor (e.g. peptide exchange factor 1) in 0.25-0.5M solution with 0.09% sodium azide.

Magnetic beads conjugated with a tetramer capture antibody in a buffered NaCl 150 mM, $Na_2HPO_4 \cdot 2H_2O$ 6.5 mM, pH 7.1-7.35 solution with added protein stabilizers and ≤0.09% sodium azide.

Fluorescently tagged antibody (e.g. tagged with FITC) that is reactive against the exiting peptide, in a buffered NaCl 150 mM, $Na_2HPO_4 \cdot 2H_2O$ 6.5 mM, pH 7.1-7.35 solution with added protein stabilizers and ≤0.09% sodium azide.

Reference exchange peptide in 10 mM DMSO solution, diluted to 1 mM in water.

Desired exchange peptide in 10 mM DMSO solution, diluted to 1-5 mM in water, or in some cases undiluted.

Assay Buffer solution, NaCl 150 mM, $Na_2HPO_4 \cdot 2H_2O$ 6.5 mM, pH 7.1-7.35, with added protein stabilizers and ≤0.09% sodium azide (1.5 mL×1 vial with natural cap). Store at 2-8° C.

Peptide Exchange Procedure: 50 µL of the tetramer solution is combined with 1 µL of peptide exchange factor, such as glycyl methionine, (resulting in a final peptide exchange factor concentration of 5-20 mM) and 1 µL of the peptide solution and the resulting solution was mixed, then incubated at room temperature for four hours.

Sandwich magnetic bead immunoassay: 20 µL capture beads is pipetted into wells 1-4 on a 96-well plate. 5 µL assay buffer is pipetted into well 2. 5 µL of exchanged tetramer is pipetted into well 4. Additional exchanged tetramers may be pipetted into wells 5 and up. The plate is protected from light and shaken for 45 min at 550 rpms/min. 150 µL of assay buffer is dispensed into each well. The plate is placed on a plate magnet and the beads are permitted to sediment for at least 5 minutes.

Separately, a preparation of the FITC-conjugated anti-tag antibody is prepared at 10 µg/mL. 25 µL of the FITC-conjugated anti-tag antibody is pipetted into each well except well 1, and the plate is again protected from light and shaken for 45 min at 550 rpms/min.

150 µL of assay buffer is dispensed into each well, and the plate is placed on a plate magnet. The beads are permitted to sediment for at least 5 minutes. The beads are resuspended in sheath fluid and transferred to labeled flow cytometer tubes (referred to herein by the number of the well they are drawn from), which are then analyzed on a flow cytometer.

Figure 1B:
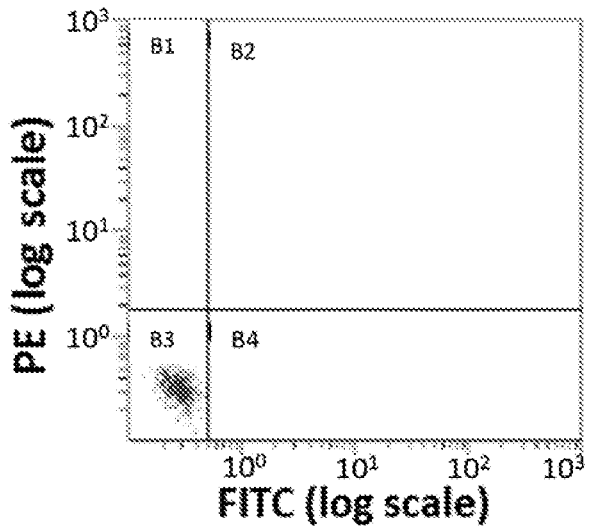
Figure 1C:
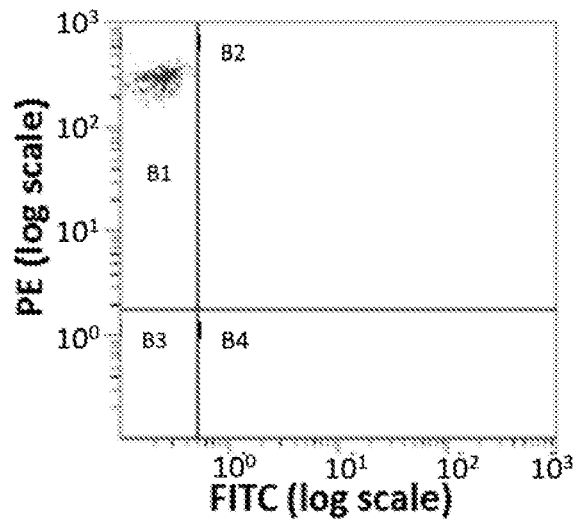
Figure 1D:
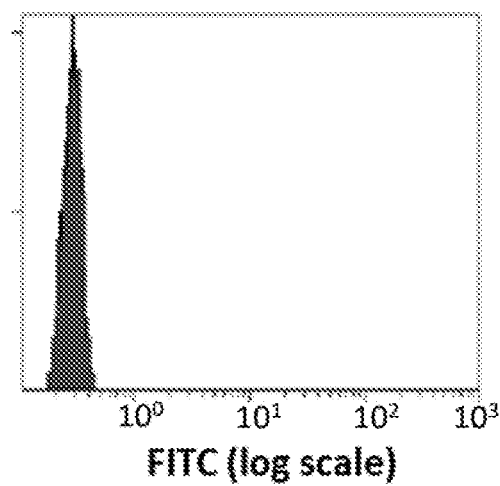
Figure 1E:
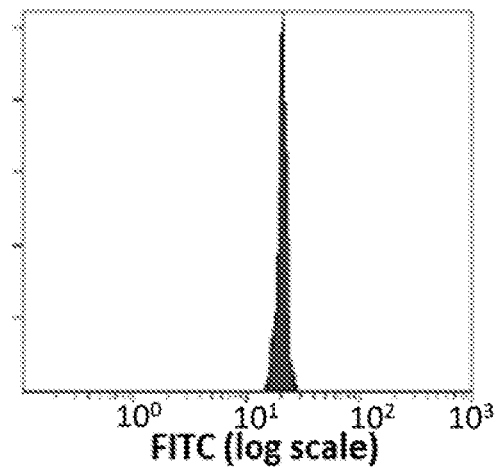
Figure 1F:
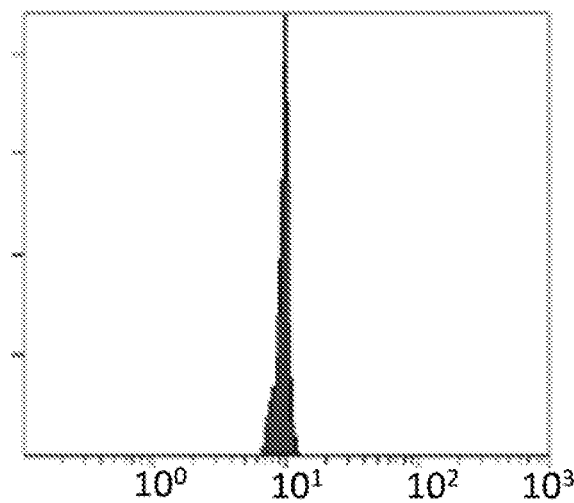

Flow Cytometry Analysis: Unused magnetic beads are used to set FSC (forward-scattered light) and SSC (side-scattered light) voltages and gains such that a live gate selects single beads and excludes doublets and larger clumps, see FIG. 1A. PMT voltages and gains are set based on the unused beads to have mean fluorescence intensities (MFI) in the first log decade (about 0.2-0.3), as seen in FIG. 1B. Tube 1 is run to perform compensation in FL1 in order to eliminate fluorochrome interference in the FITC channel, see FIG. 1C. The FL1 MFI is set to the first log decade, close to that obtained with beads only. Tube 2, which contains beads that have captured no tetramer and therefore no tagged peptide, is run to calibrate the level for 0% tagged peptide, i.e. 100% peptide exchange (see FIG. 1D). In the exemplary data provided here, the MFI is 0.287. Tube 3, which contains a solution where all tetramers display the original tagged peptide, is run to calibrate the level for 100% tagged peptide, i.e. 0% peptide exchange (see FIG. 1E). In the exemplary data provided here, the MFI is 20.4. Tubes 4 and up are run to evaluate the samples. Peptide exchanged tetramers will display various quantities of tagged peptides, depending on their binding affinities to HLA-A*02:01 molecules. Therefore, the FL1 MFI measured will be intermediary between MFI values obtained with tubes 2 and 3. See FIG. 1F, where in the exemplary data provided here, the MFI is 9.37. The control data can then be interpolated to find the percent of tagged peptide in the sample, as shown in Table 1.

TABLE 1

Exemplary Calculation of Peptide Exchange Rate

| Analyzed sample | MFI | % of tagged peptide | % peptide exchange |
|---|---|---|---|
| 0% peptide binding ctrl | 0.287 | 0 | 100 |
| 100% peptide binding ctrl | 20.4 | 100 | 0 |
| Peptide exchange with 1 µM test peptide | 9.37 | 45.2 | 54.8 |

Figure 4:
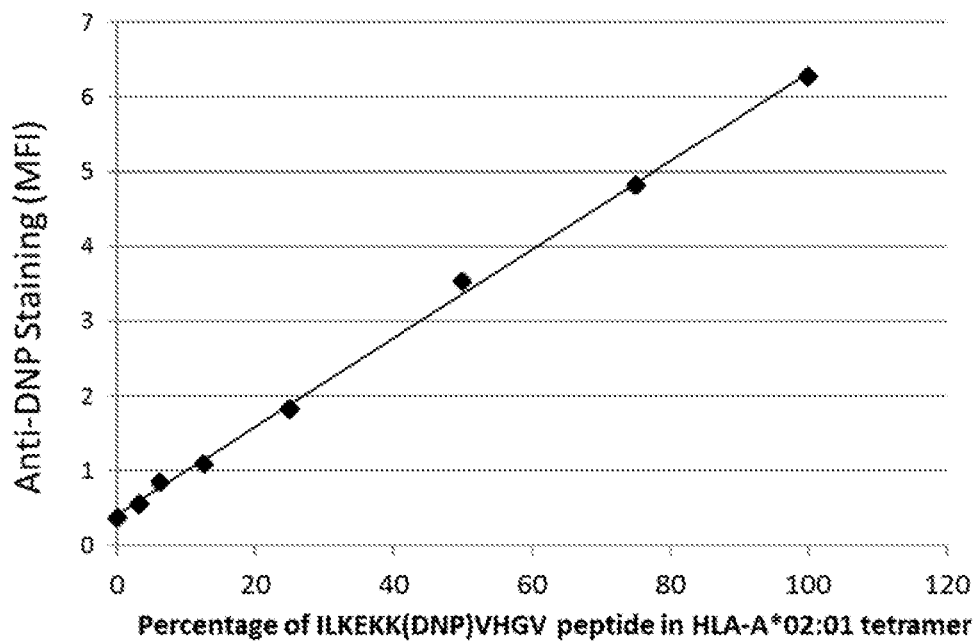
FIG. 4 shows a linear correlation between anti-DNP signals measured by flow cytometry and actual exiting DNP-tagged peptide levels. Figure discloses SEQ ID NO: 3.

Example 2: Detection of Exiting Peptide with FITC-Conjugated DNP-Specific Antibodies Accurately Measures Peptide Exchange HLA-A*02:01 tetramers were built with various ratios of peptides ILKEKK(DNP)VHGV (SEQ ID NO: 3) and ILKEPVHGV (SEQ ID NO: 13). They were captured with anti HLA-ABC antibody-conjugated beads and stained with FITC conjugated anti DNP. Mean fluorescence intensities in FL1 were collected on a flow cytometer and plotted versus ILKEKK(DNP)VHGV (SEQ ID NO: 3) percentages. The results, provided in FIG. 4, indicate that there is a linear correlation between anti-DNP signals measured by flow cytometry and actual exiting DNP-tagged peptide levels.

Figure 5:
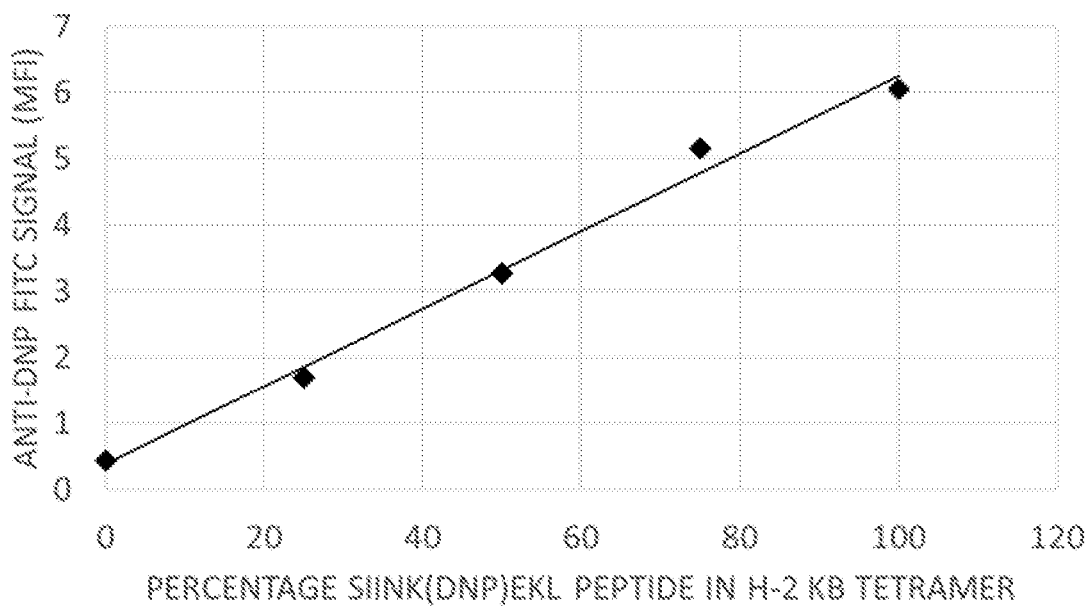
FIG. 5 shows a linear correlation between anti-DNP signals measured by flow cytometry and actual DNP antigens captured. Figure discloses SEQ ID NO: 7.

Example 3: Detection of DNP with FITC Conjugated DNP Specific Antibody Accurately Measures Peptide Exchange in H-2 Kb Tetramers H-2 Kb tetramers were built with various ratios of peptides SIINFEKL (SEQ ID NO: 50) and SIINK(DNP)EKL (SEQ ID NO: 7). They were captured with anti H-2 Kb antibody conjugated beads and stained with FITC conjugated anti DNP. Mean fluorescence intensities in FL1 were collected and plotted versus SIINK(DNP)EKL (SEQ ID NO: 7) percentages. The results, depicted in FIG. 5, indicate that there is an exact linear correlation between anti-DNP signals measured by flow cytometry and actual DNP antigens captured.

Example 4: Selection of Exiting Peptide Sequence

Figures 6, 7:
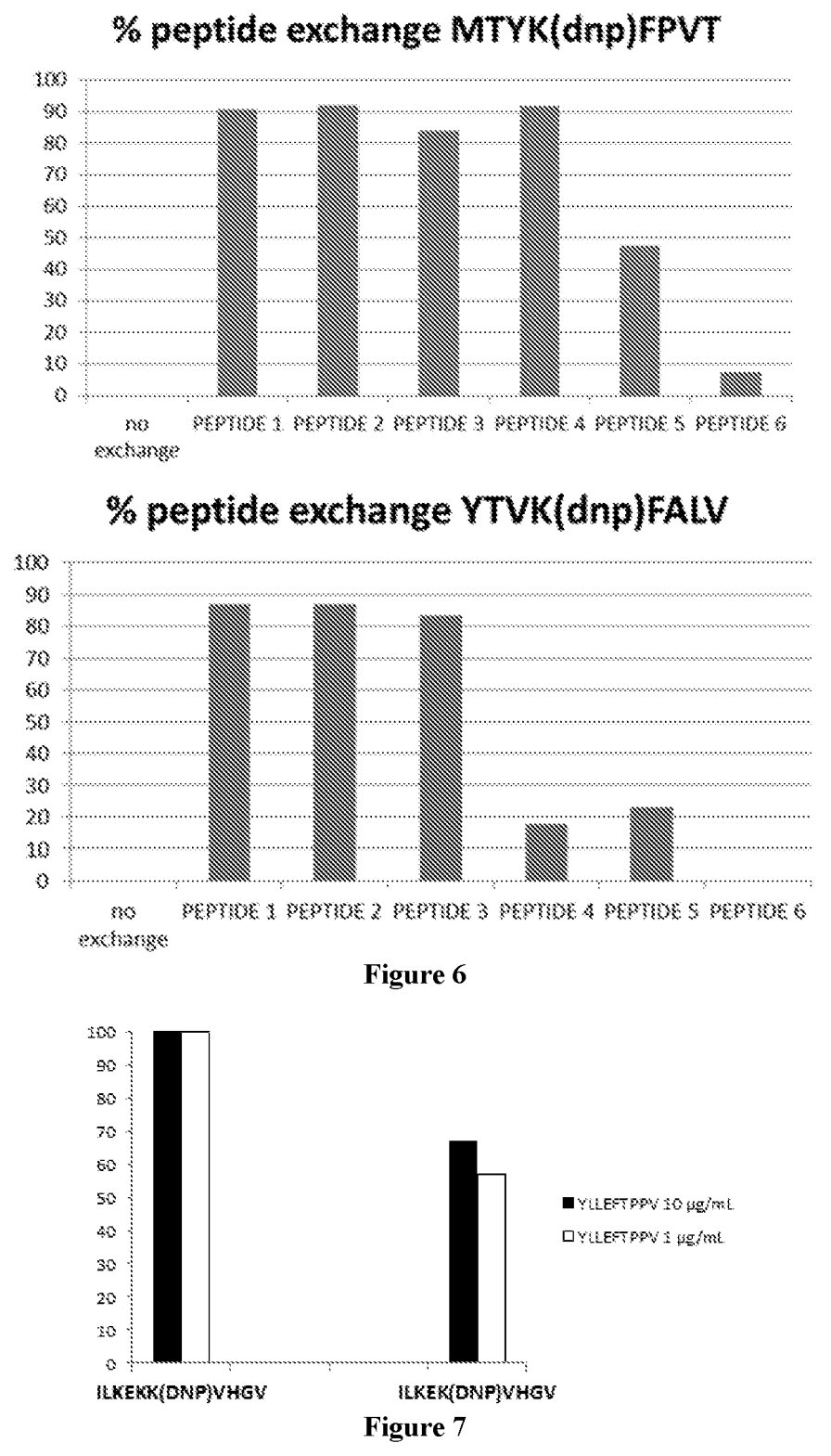

Peptide exchange was performed using two H-2 Kb tetramers at 280 jig/mL that were made with peptides MTYK(DNP)FPVT (SEQ ID NO: 1) and YTVK(DNP)FALV (SEQ ID NO: 2). Exchange was performed in the presence of competing peptides at 10 µg/mL. Tetramers were captured with beads conjugated with an anti H-2 Kb specific antibody. Detection was performed with a FITC-conjugated anti-DNP antibody at 10 µg/mL. The results are depicted in FIG. 6, where the exiting peptides are labeled as follows:

| Label | Peptide |
|---|---|
| Peptide 1 | ISHNFCNL (SEQ ID NO: 51) |
| Peptide 2 | LTFNYRNL (SEQ ID NO: 52) |
| Peptide 3 | FSPAFDNL (SEQ ID NO: 53) |
| Peptide 4 | RCQIFANI (SEQ ID NO: 54) |
| Peptide 5 | CRPRFREL (SEQ ID NO: 55) |
| Peptide 6 | PGCAFLTV (SEQ ID NO: 56) |

Tetramers built with MTYK(DNP)FPVT (SEQ ID NO: 1) allowed exchange with a wide range of peptides, which was not possible with exiting peptide YTVK(DNP)FALV (SEQ ID NO: 2).

Example 5: Comparison of Exiting Peptide Sequences

Peptide exchange was performed using two HLA-A*02:01 tetramers at 280 µg/mL made with peptides ILKEKK(DNP)VHGV (SEQ ID NO: 3) and ILKEK(DNP)VHGV (SEQ ID NO: 4). Exchange was performed in the presence of GM (glycine-methionine) 10 mM and high-affinity competing peptide YLLEFTPPV (SEQ ID NO: 5) at 10 and 1 µg/mL. Tetramers were captured with beads conjugated with an anti HLA-ABC specific antibody at 10 µg/mL. The results, depicted in FIG. 7, suggest that tetramers built with ILKEKK(DNP)VHGV (SEQ ID NO: 3) performs better in peptide exchange.

Example 6: Use of Exchanged Tetramers for Cell Staining

Figure 2A:
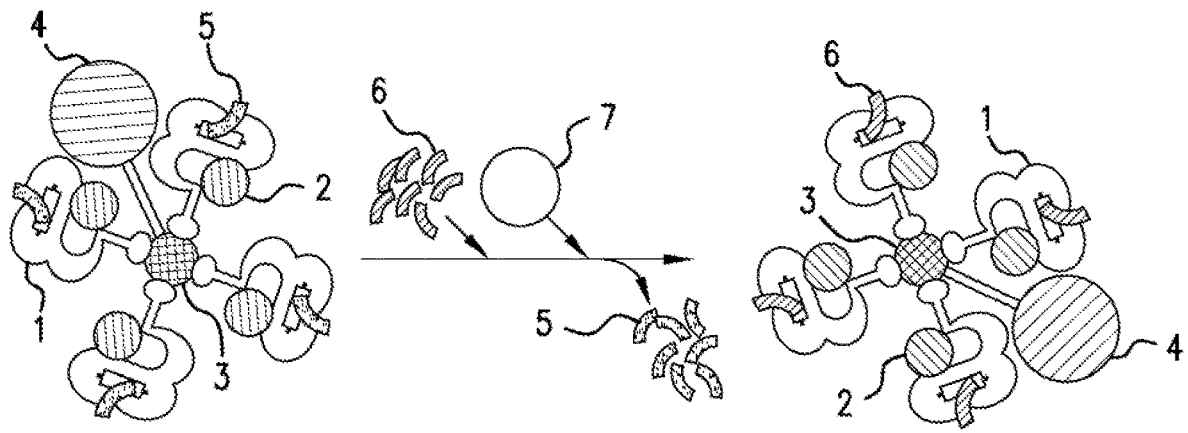
FIG. 2A is a schematic depiction of an exemplary peptide exchange.
Figure 2B:
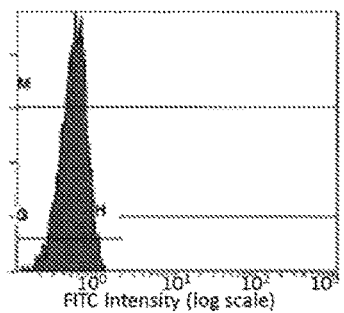
FIG. 2B shows that the tetramers obtained by peptide exchange stain cells just like tetramers originally prepared with Mart-1 peptide.
Figure 2B:
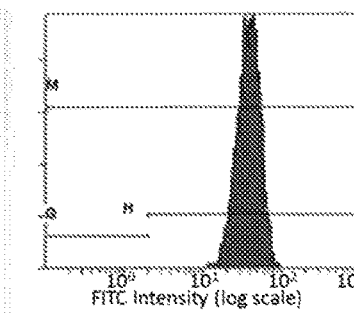
Figure 2B:
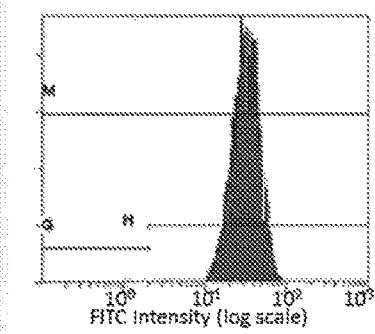

HLA-A*02:01 tetramers built with peptides RMFNAPYL (SEQ ID NO: 57) (shown in this example) as well as peptides RMYSYVATL (SEQ ID NO: 58), ILKEK(DNP)VHGV (SEQ ID NO: 4) and ILKEKK(DNP)VHGV (SEQ ID NO: 3) were incubated for four hours with competing peptide Mart-1 (ELAGIGILTV (SEQ ID NO: 12)) 1-100 µg/mL, with exchange factor glycine-methionine 10 mM, as schematically depicted in FIG. 2A. MHC proteins are formed by the combination of the a subunit (1) and the β subunit (2). The MHC proteins are tetramerized by attachment to a streptavidin (3). The tetrameric MHC complex is labeled (here, with a fluorophore) (4). Bound to each MHC protein in the complex is the exiting peptide (5). For the exchange, entering peptide (6) and peptide exchange factor (7) are added. The exiting peptide (5) is displaced. The resulting complex contains the entering peptide (6) bound to the MHC proteins. The exchanged tetramers were then used for cell staining, and compared to tetramers originally folded with Mart-1 peptide (i.e., without peptide exchange). As shown in FIG. 2B, the tetramers obtained by peptide exchange stained cells just as the tetramers originally prepared with Mart-1 peptide.

Example 7: Comparison of Exchange Rates with Different Fluorophores

50 µL of MHC Tetramers (H-2 Kb PE, H-2 Kb APC or H-2 Kb BV421) with exiting peptide TFQRK(DNP)PAAF (SEQ ID NO: 16) were mixed with 1 µL of 0.25 M Peptide Exchange Factor (glycyl-methionine) and 1 µL of 1 mM or 0.1 mM reference entering peptide (SIYRYYGL (SEQ ID NO: 59)). The mixtures were incubated for 4 hours at room temperature, protected from light.

20 µL of magnetic capture beads were added to wells of a v-bottom 96-well plate for each tested peptide plus wells for control samples. Each test well received 5 µL from the peptide exchange samples. The plate was shaken for 45 minutes at 550 rpm, room temperature, protected from light. After bead rinse, wells received 25 µL of 1× exiting peptide antibody. The plate was shaken for 45 minutes at 550 rpm, room temperature, protected from light. Beads were rinsed, resuspended in 1× assay buffer and run on a FC500 Flow Cytometer. Single beads were gated on FSC vs. SSC and MFI were measured on 500 events per test. Peptide exchange rate was calculated using a calibration curve generated with MFI values from controls. The results are shown in Table 2:

TABLE 2

Exchange Rates with Various Fluorophores

|  | PE | BV421 | APC |
| --- | --- | --- | --- |
| Reference Peptide 20 µM | 100 | 97.34 | 99.13 |
| Reference Peptide 2 µM | 92.72 | 90.56 | 97.08 |
| No Reference Peptide | 16 | 13.3 | 30.35 |

Example 8: Comparison of HLA-A*02:01 Peptide Exchange Quantitation and Predicted Affinity Random peptides of different predicted HLA-A*02:01 binding affinities were added to exchangeable HLA-A*02:01 tetramers with exiting peptide ILKEKK(DNP)VHGV (SEQ ID NO: 3) at a final 20 µM concentration. Peptide exchange data were obtained after incubating peptides (20 µM final) with tetramer for 4 hours, then followed by capture with anti HLA-ABC beads and staining with an anti-DNP FITC antibody.

Figure 8:
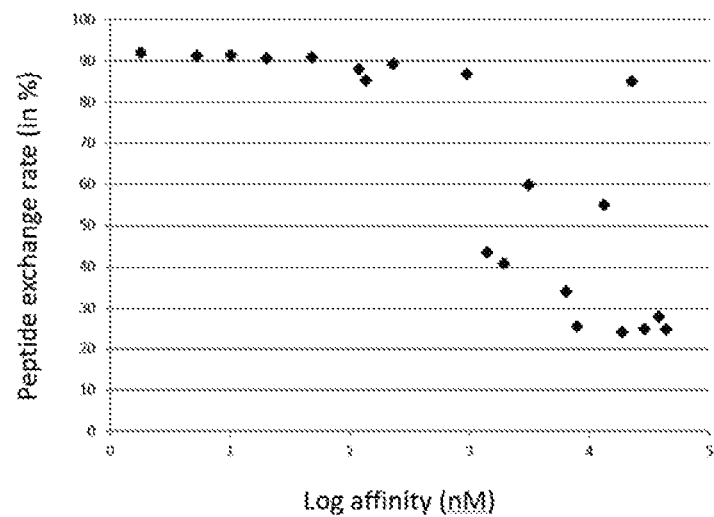
FIG. 8 plots the measured peptide exchange rate for various peptides against their predicted affinities.

Peptides with predicted affinities varying from 1 nM to 1000 nM were swapped at a high rate (in the 90% range). Lower binding affinity (>1000 nM) peptides triggered lower peptide exchanges (60-20%). However, several peptides of predicted low affinities showed high exchange rates. The results are presented in Table 3 and FIG. 8.

TABLE 3

|  | % peptide exchange | affinity (nM) | log affinity (nM) |
| --- | --- | --- | --- |
| HLA-A*02:01Reference peptide, YLLEFTPPV (SEQ ID NO: 5) | 91.9 | 1.8 | 0.26 |
| FLYDDNQRV (SEQ ID NO: 33) | 91.2 | 5.24 | 0.72 |
| GLADQLIHL (SEQ ID NO: 23) | 91.4 | 10.08 | 1.00 |
| AVLDGLLSL (SEQ ID NO: 34) | 90.7 | 20.23 | 1.31 |
| GLAVVTHGL (SEQ ID NO: 24) | 91.0 | 48.07 | 1.68 |
| WMHKVPASL (SEQ ID NO: 35) | 87.9 | 118.33 | 2.07 |
| CINGVCWTV (SEQ ID NO: 36) | 85.3 | 135.48 | 2.13 |
| WMHHNMDLI (SEQ ID NO: 37) | 89.2 | 229.38 | 2.36 |
| SLPPPGTRV (SEQ ID NO: 38) | 86.6 | 946.37 | 2.98 |
| LTLGEFLKL (SEQ ID NO: 39) | 43.6 | 1413.34 | 3.15 |
| IMQLMPFGC (SEQ ID NO: 40) | 40.9 | 1924.6 | 3.28 |
| IMQIMPYGC (SEQ ID NO: 41) | 59.9 | 3132.04 | 3.50 |
| RIKDFLRNL (SEQ ID NO: 42) | 34.0 | 6422.34 | 3.81 |
| ALLAVGATK (SEQ ID NO: 43) | 25.7 | 7937.43 | 3.90 |
| CSLWNGPHL (SEQ ID NO: 44) | 55.2 | 13299.06 | 4.12 |
| EYILSLEEL (SEQ ID NO: 45) | 24.2 | 18577.45 | 4.27 |
| ALALEVGEL (SEQ ID NO: 46) | 85.1 | 22436.49 | 4.35 |
| SYVPSAEQI (SEQ ID NO: 47) | 25.0 | 28307.28 | 4.45 |
| ATVQGQNLK (SEQ ID NO: 48) | 27.9 | 38208.35 | 4.58 |
| IRLRPGGKK (SEQ ID NO: 49) | 25.0 | 43925.21 | 4.64 |

The peptide exchange quantification assays provided herein are useful to screen good HLA-A*02:01 binding peptides and to verify high rates of peptide exchange.

Example 9: HLA-A*24:02 Tetramer Made with Exiting Peptide TFQRK(DNP)PAAF (SEQ ID NO: 16) is Amenable to Peptide Exchange Random peptides of different predicted HLA-A*02:01 binding affinities were added to exchangeable HLA-A*24:02 tetramers with exiting peptide TFQRK(DNP)PAAF (SEQ ID NO: 16) at a final 20 µM concentration. Peptide exchange data were obtained after incubating peptides (20 µM final) with tetramer for 4 hours, then followed by capture with anti HLA-ABC beads and staining with an anti-DNP FITC antibody.

Figure 9:
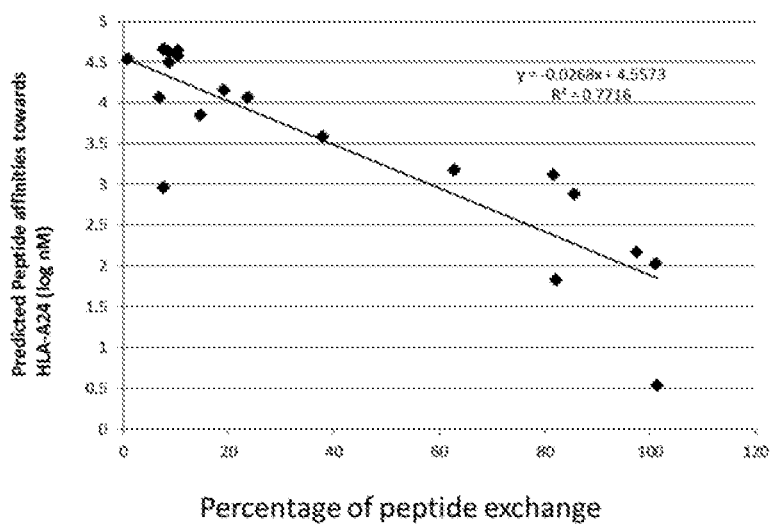
FIG. 9 plots the predicted affinities for various peptides against their measured peptide exchange rate.
Figure 10A:
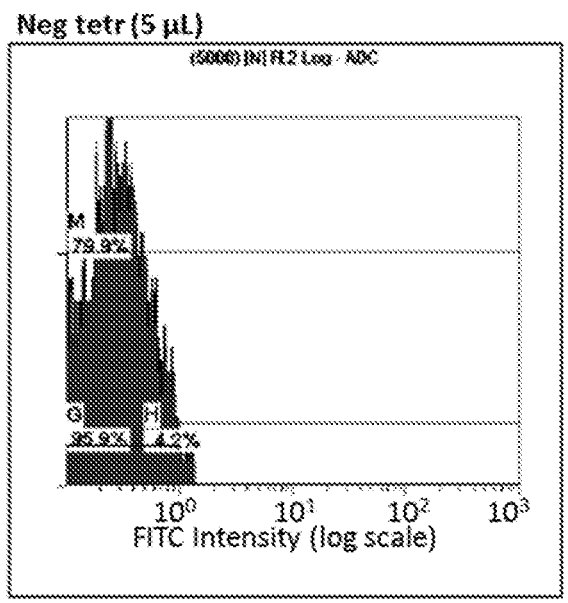
FIGS. 10A-J show the reactivity of natural and exchanged tetramers used to stain insect cells expressing the T cell receptor for the complex HLA-A*24:02/QYDPVAALF (SEQ ID NO: 6).
Figure 10B:
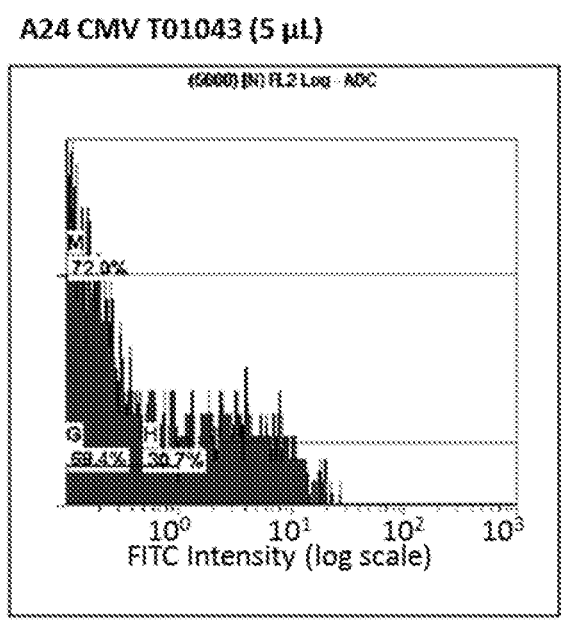
Figure 10C:
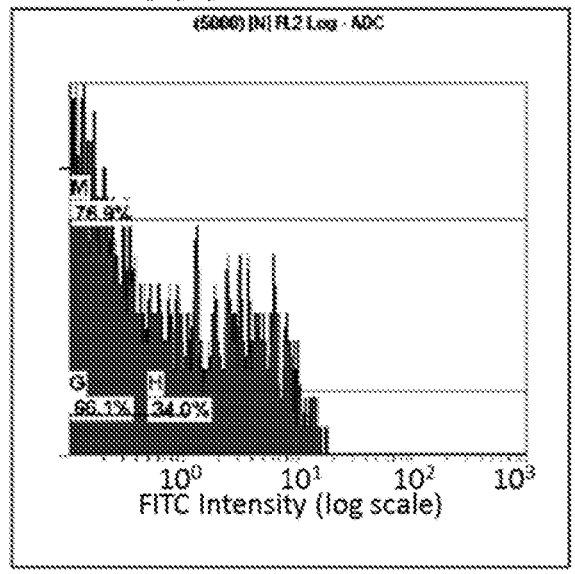
Figure 10D:
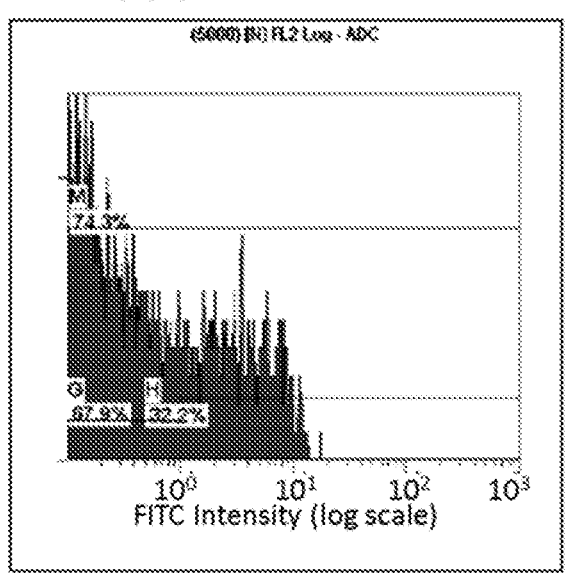
Figure 10E:
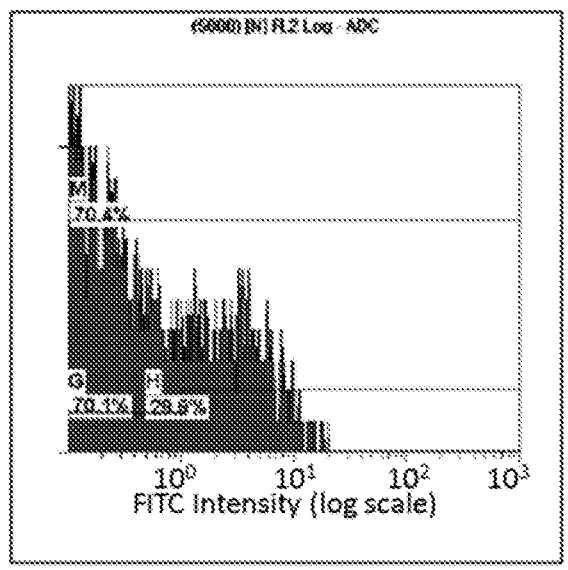
Figure 10F:
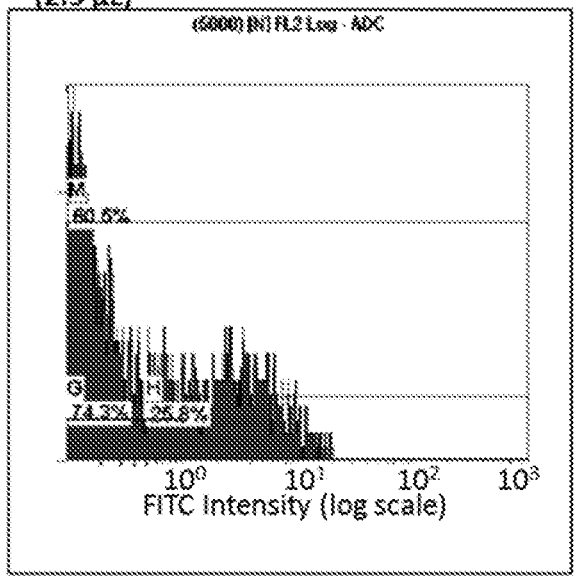
Figure 10G:
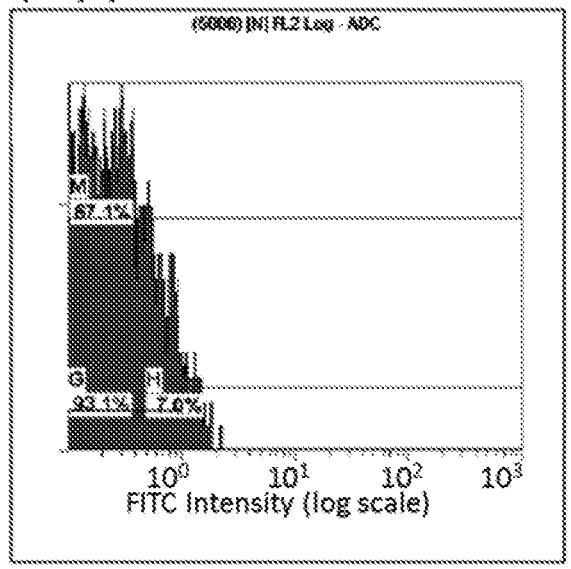
Figure 10H:
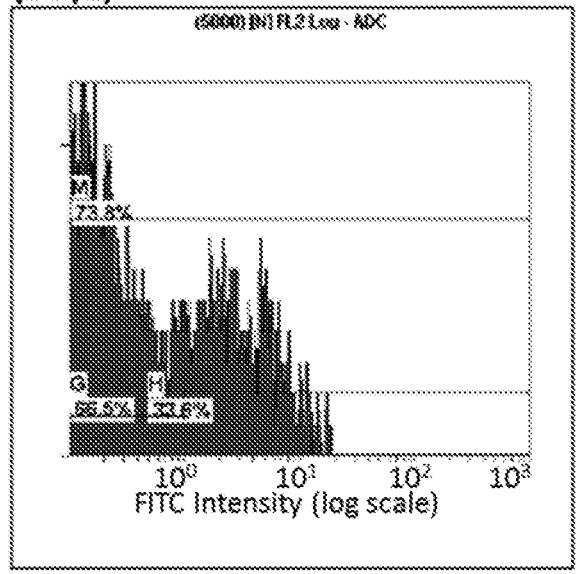
Figure 10I:
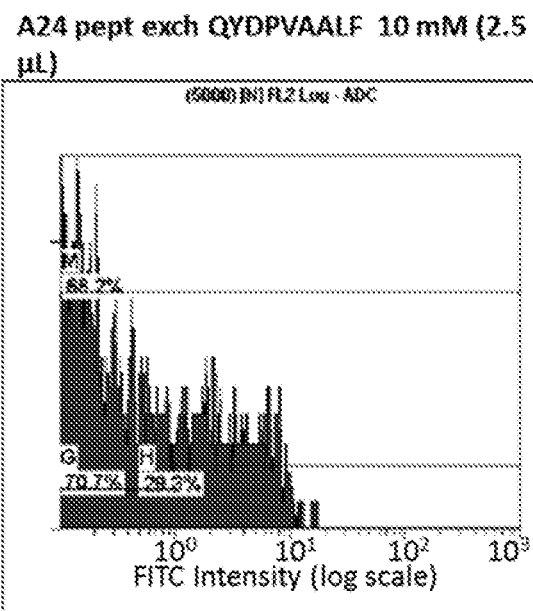
Figure 10J:
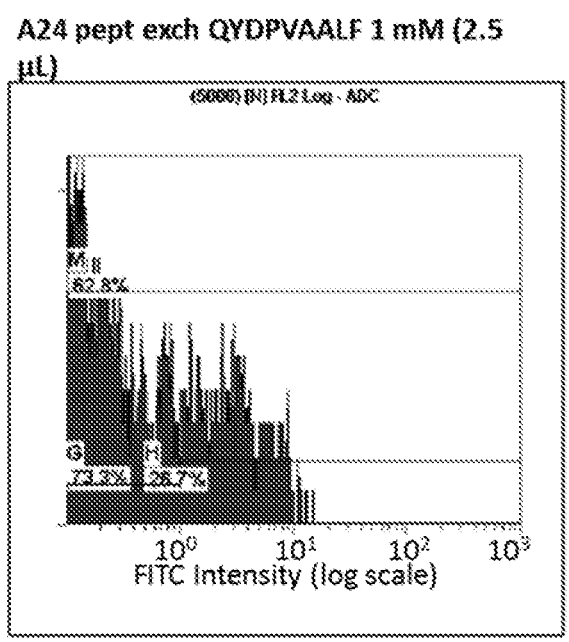

Predicted peptide binding affinities towards HLA-A*24:02 and peptide exchange rate on HLA-A*24:02 tetramers were correlated with the exception of a few outliers, as shown in FIG. 9 and Table 4.

TABLE 4

| Competing peptide | % Peptide Exchange | HLA-A*24:02 binding affinity (nM) | HLA-A*24:02 binding affinity (log nM) |
| --- | --- | --- | --- |
| AMAPRTLLL (SEQ ID NO: 18) | 81.62 | 1294.73 | 3.11 |
| ATDALMTGY (SEQ ID NO: 19) | 7.74 | 45973.84 | 4.66 |
| EVDPIGHLY (SEQ ID NO: 20) | 8.60 | 42594.17 | 4.63 |
| FLSELTQQL (SEQ ID NO: 21) | 23.65 | 11900.16 | 4.08 |
| FMYSDFHFI (SEQ ID NO: 22) | 7.74 | 928.76 | 2.97 |
| GLADQLIHL (SEQ ID NO: 23) | 0.86 | 35160.21 | 4.55 |
| GLAVVTHGL (SEQ ID NO: 24) | 8.60 | 30939.23 | 4.49 |
| GYSLKLSKL (SEQ ID NO: 25) | 37.93 | 3883.92 | 3.59 |

TABLE 4-continued

| Competing peptide | % Peptide Exchange | HLA-A*24:02 binding affinity (nM) | HLA-A*24:02 binding affinity (log nM) |
|---|---|---|---|
| IMDQVPFSV (SEQ ID NO: 26) | 6.88 | 11764.46 | 4.07 |
| IYSTVASSL (SEQ ID NO: 27) | 100.98 | 107.78 | 2.03 |
| LNMADKKET (SEQ ID NO: 28) | 10.32 | 44685.98 | 4.65 |
| RAHYNIVTF (SEQ ID NO: 29) | 85.58 | 763.13 | 2.88 |
| RVRAYTYSK (SEQ ID NO: 30) | 10.32 | 37239.02 | 4.57 |
| RYMRWTYRF (SEQ ID NO: 31) | 101.29 | 3.46 | 0.54 |
| SLYNTVATL (SEQ ID NO: 32) | 14.62 | 7140.89 | 3.85 |

Example 10: HLA-A*24:02 Tetramers Generated by Peptide Exchange have the Same Cell Reactivity as the Ones Generated by Folding 50 µL of HLA-A*24:02 Tetramer with exiting peptide TFQRK(DNP)PAAF (SEQ ID NO: 16) was mixed with 1 µL of 0.25 M Peptide Exchange Factor (glycyl-methionine) and 1 µL of 1 mM or 0.1 mM CMV peptide QYDPVAALF (SEQ ID NO: 6). The mixture was incubated for 4 hours at RT, protected from light. S2 insect cells expressing the T cell receptor for the complex HLA-A*24:02/QYDPVAALF (SEQ ID NO: 6) were resuspended at 5×10⁶ cells per mL in PBS containing 0.2% BSA and 0.1% NaN3. 100 µL of cells were incubated for 30 minutes at room temperature with 2.5 or 5 µL of tetramer, either negative control tetramer (PN T01044), commercial HLA-A*24:02 CMV QYDPVAALF (SEQ ID NO: 6) PE Tetramer (T01043) or HLA-A*24:02 CMV QYDPVAALF (SEQ ID NO: 6) PE Tetramer obtained by peptide exchange. After a wash with PBS containing 0.2% BSA and 0.1% NaN3, cells were resuspended in 400 µL of PBS containing 0.5% formaldehyde and then were analyzed on an FC500 flow cytometer. The data, presented in FIG. 10, shows that the commercial HLA-A*24:02 CMV QYDPVAALF (SEQ ID NO: 6) PE Tetramer (T01043) is indistinguishable from the HLA-A*24:02 CMV QYDPVAALF (SEQ ID NO: 6) PE Tetramer obtained by peptide exchange.

Example 11: Exchange of Peptides on MHC Class II Tetramer

Figure 11:
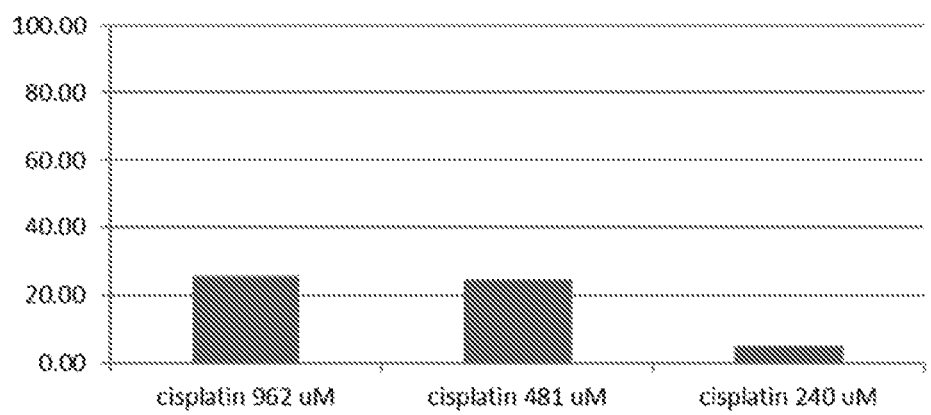
FIG. 11 shows peptide exchange results on an MHC Class II allele, HLA-DR4.

A 50 µL sample of PE conjugated MHC class II DRB1*04:01 tetramer with exiting peptide sequence K(Dnp)LPKPPKPVSKMRMATPLLMQALPM (SEQ ID NO: 60) was incubated with 2 µL of 24.1 mM, 12.05 mM and 6.025 mM cisplatin for 3 hours at room temperature in the dark. Quantification of cisplatin-triggered peptide replacement was done with a Flow Cytometric Sandwich Immunoassay. 20 µL of anti HLA DR-conjugated magnetic capture beads were added to wells of a v-bottom 96-well plate for each tested cisplatin dilution plus wells for control samples. Each test well received 5 µL from the cisplatin treated samples. The plate was shaken for 45 minutes at 550 rpm, room temperature, protected from light. After bead rinse, wells received 25 µL of 1× exiting peptide antibody. The plate was shaken for 45 minutes at 550 rpm, room temperature, protected from light. Beads were rinsed, resuspended in 1× assay buffer and run on a FC500 Flow Cytometer. Single beads were gated on FSC vs. SSC and MFI were measured on 500 events per test. Peptide exchange rate was calculated using a calibration curve generated with MFI values from controls. The results are depicted in FIG. 11.

Example 12: Determination of the Biological Activity of a Vaccine

The methods described herein were evaluated to determine whether they could detect the biological activity of a vaccine. The tested vaccine was DPX-Survivac, an ovarian cancer vaccine candidate that includes several survivin peptide antigens that are each restricted to a different human class I allele. One of the peptides in the vaccine is SurA2.M, a HLA-A2-restricted peptide. The peptides used in the study are listed in Table 4, with their affinities to HLA-A2 calculated by the IEDB artificial neural network method.

TABLE 5

Peptides Used in Vaccine Study

| Name | Sequence | HLA Restriction | HLA-A2 Affinity (nM) |
|---|---|---|---|
| SurA1.T | FTELTLGEF (SEQ ID NO: 61) | HLA-A1 | 14587.88 |
| SurA2.M | LMLGEFLKL (SEQ ID NO: 62) | HLA-A2 | 25.41 |
| SurA3.K | RISTFKNWPK (SEQ ID NO: 63) | HLA-A3 | 24220.66 |
| SurA24 | STFKNWPFL (SEQ ID NO: 64) | HLA-A24 | 243.83 |
| SurB7 | LPPAWQPFL (SEQ ID NO: 65) | HLA-B7 | 16536.16 |
| Y9T | YMLDLQPET (SEQ ID NO: 66) | HLA-A2 | 21.23 |
| Y10T | YMLDLQPETT (SEQ ID NO: 67) | HLA-A2 | 176.26 |
| A16L | AQYIKANSKFIGITEL (SEQ ID NO: 68) | N/A | 22215.71 |

The quantified peptide exchange described herein was compared to established methods for quantifying the biological activity of a vaccine.

Quantified Peptide Exchange Assay: HLA-A*02:01 Tetramers were prepared containing exiting peptide ILKEKK(DNP)VHGV (SEQ ID NO: 3). Peptide exchange was performed against (a) the peptide prepared individually in a buffered solution or (b) in the DPX-Survivac vaccine prepared in an aqueous formulation. HLA-A*02:01 tetramer, and peptide exchange factor glycylmethionine were mixed with each peptide to be tested. Peptide exchange was then quantified by the flow cytometric sandwich immunoassay using magnetic capture beads.

Figure 12A:
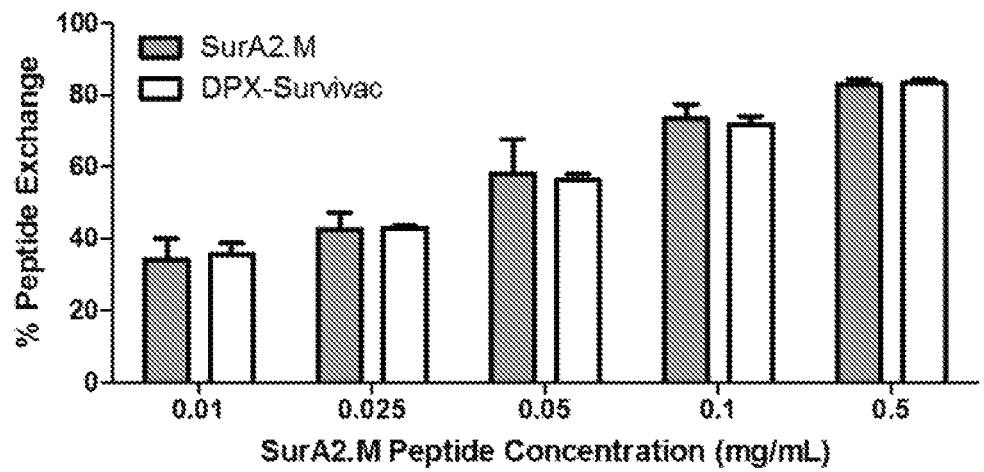
FIGS. 12A-12E show the results of peptide exchange in a complex mixture (a vaccine) and compare the results to a cell-based T2 shift assay and an animal-based IFN-γ ELISPOT assay.

This comparison, shown in FIG. 12A, shows that that peptide exchange rate of SurA2.M is not statistically distinguishable whether it is dissolved individually in a buffered solution or mixed with other components of the vaccine. Data shown as an average±SEM of three independent repeats. Student's t-test was performed to compare the levels of peptide exchange for DPX-Survivac to that for SurA2.M peptide at each concentration level; no statistical differences were detected at p<0.05.

This result may be dependent on the affinity of the peptide for HLA-A2. Thus, by optimizing a concentration curve using individual peptides, HLA-A*02:01 MHC proteins may be used to quantify the concentration of HLA-A2 restricted peptides in simple solutions or more complex formulations.

Figure 12B:
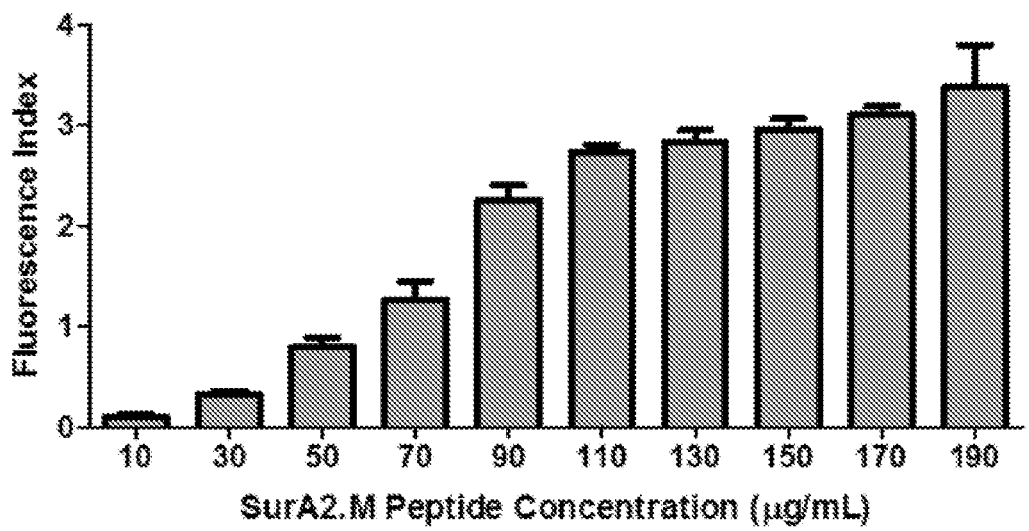

T2 HLA-A2 Shift assay: T2 cells are a human cell line that express low levels of HLA-A2 on their surface due to deficiency in TAP protein. Upon incubation with a peptide that can bind to HLA-A2, expression of HLA-A2 on the surface increases as the peptide stabilizes the complex. Immunofluorescent staining of T2 cells using a fluorescein-conjugated monoclonal antibody (anti-HLA-A2) is used to quantify the relative expression of HLA-A2 in vitro after antigen stimulation. In this study, T2 cells were stimulated with various amounts of peptide for 24 h; HLA-A2 surface expression was detected using BB7.2-PE anti-HLA-A2 antibody quantified using BD FACSCalibur. The results, presented in FIG. 12B, show that the response range for this assay is between 10-110 μg/mL. Data are presented as an average±SEM of three independent experiments and expressed relative to the unstimulated control.

Figure 12C:
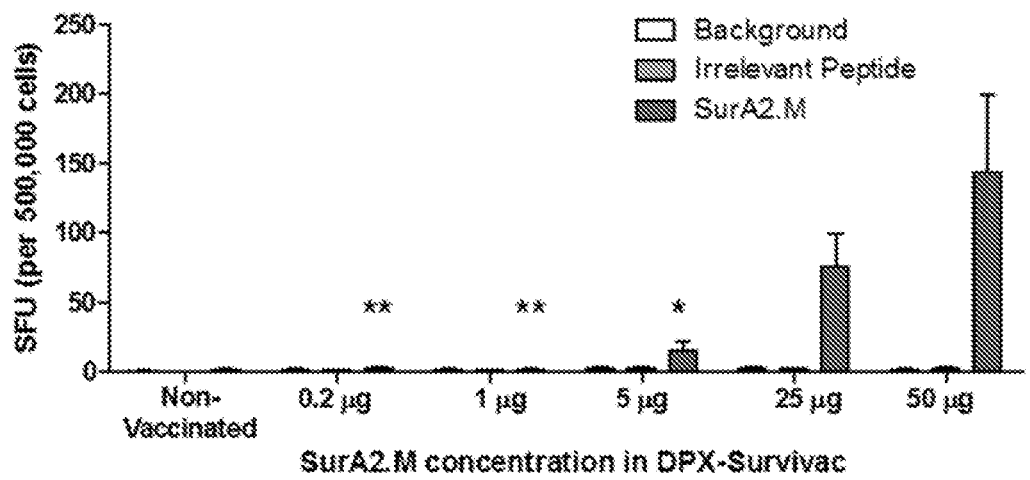

IFN-γ ELISPOT Assay: HLA-A2 transgenic mice (HHD, n=6) were vaccinated with DPX-Survivac formulated with decreasing doses of the HLA-A2 restricted peptide SurA2.M. Eight days after vaccination, mice were terminated and spleens collected. Splenocytes were stimulated in an IFN-γ ELISPOT plate with media (background), an irrelevant HLA-A2 restricted peptide or with SurA2.M peptide. Plates were developed after 18 hours and spot forming units (SFU) were quantified using Immunospot Reader (C.T.L.). The results, presented in FIG. 12C, show a dose response was observed. Statistics were performed to compare the response of each dose to the maximum, 50 μg, by 1-way ANOVA followed by Dennett's post-test; *p<0.05, **p<0.01. The IFN-γ ELISPOT Assay can detect 90% degradation of SurA2.M in the vaccine.

Figure 12D:
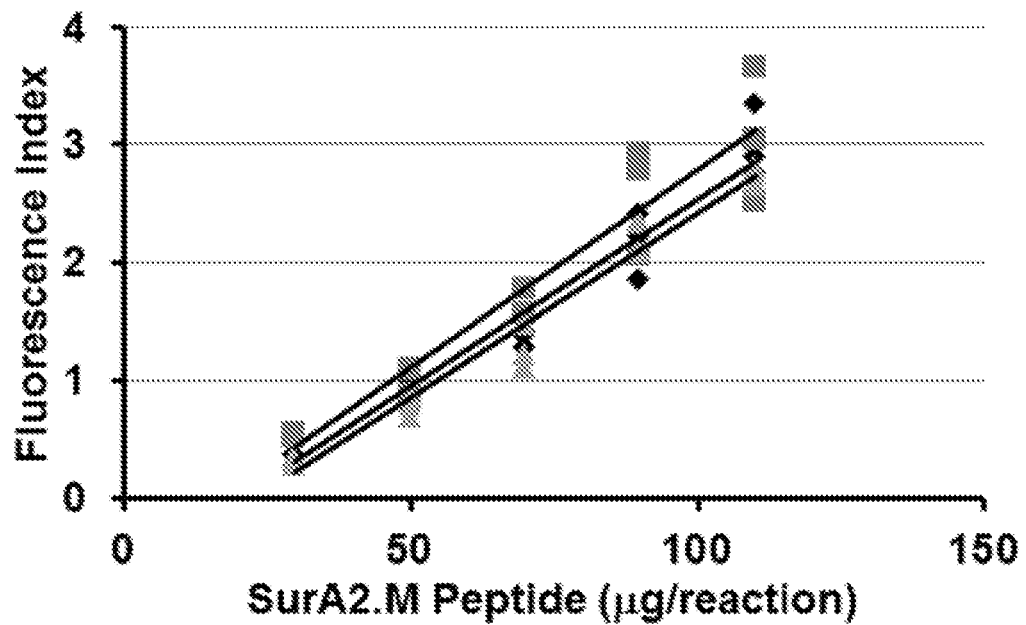
Figure 12E:
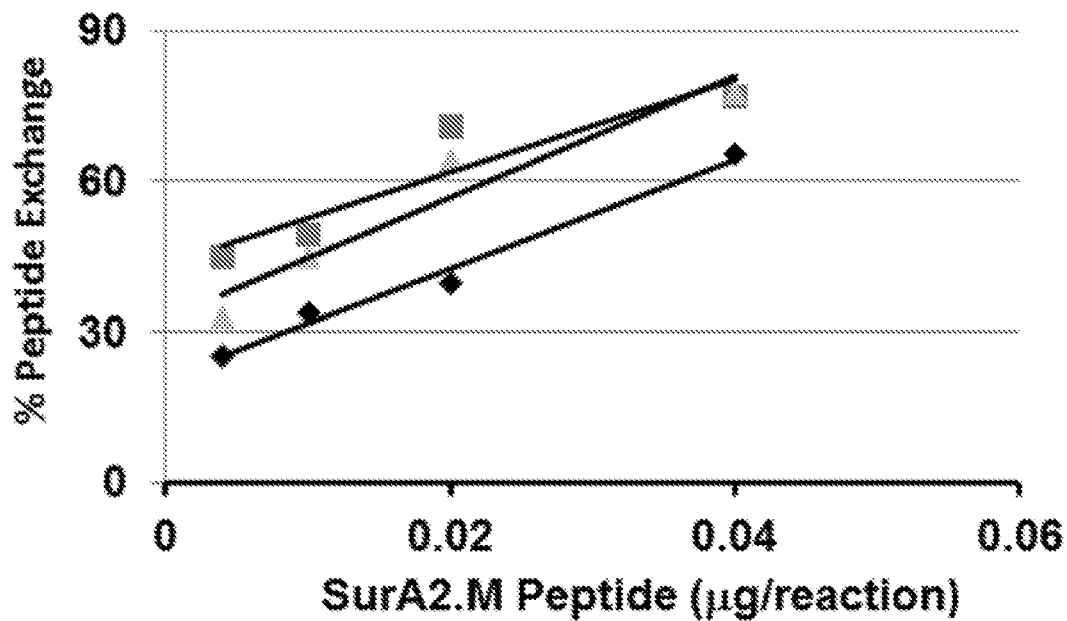

Comparison of Peptide Exchange Assay to T2 HLA-A2 Shift assay: The peptide exchange assay described herein and the T2 HLA-A2 shift assay were conducted on various amounts of peptide per reaction. The results are presented in FIGS. 12D (T2 HLA-A2 shift assay) and 12E (peptide exchange assay), with the three independent repeats shown in diamonds, squares, and triangles. The T2 Shift assay provides a high degree of linearity when applied to the samples containing 10 μg/reaction to 110 μg/reaction of SurA2.M peptide. The peptide exchange assay had an upper limit of quantification below 0.2 μg/reaction and the response range, with an acceptable degree of linearity, was 0.004 μg/reaction to 0.04 μg/reaction.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

1. Altman J D, Davis M M. MHC-peptide tetramers to visualize antigen-specific T cells. Curr Protoc Immunol. 2003; 17(17):13
2. Toebes M, et al. (2006) Design and use of conditional MHC class I ligands. Nat Med 12(2):246-251.
3. Rodenko B, Toebes M, Celie P H, Perrakis A, Schumacher T N: Ovaa H: Class I major histocompatibility complexes loaded by a periodate trigger. J Am Chem Soc 2009, 131:12305-12313.
4. Saini S K, Schuster H, Ramnarayan V R, Rammensee H G, Stevanović S, Springer S. Dipeptides catalyze rapid peptide exchange on MHC class I molecules. Proc Natl Acad Sci USA. 2015 112(1):202-7.
5. Luft, T. et al. Exogenous peptides presented by transporter associated with antigen processing (TAP)-deficient and TAP-competent cells: intracellular loading and kinetics of presentation. J. Immunol. 167, 2529-2537 (2001).

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A kit for quantified peptide exchange comprising an MHC molecule bound to a first peptide, wherein the first peptide is labeled with DNP, wherein the quantified peptide exchange comprises exchanging the first peptide with a second peptide, and wherein (1) the MHC molecule is HLA-A*02:01 and the first peptide is ILKEKK(DNP)VHGV (SEQ ID NO: 3) or ILKEK(DNP)VHGV (SEQ ID NO: 4); or (2) the MHC molecule is H-2Kb and the first peptide is SIINK(DNP)EKL (SEQ ID NO: 7), MTYK(DNP)FPVT (SEQ ID NO: 1), or YTVK(DNP)FALV (SEQ ID NO: 2).

2. The kit of claim 1, further comprising an anti-DNP antibody.

3. The kit of claim 1, further comprising a capture system comprising (1) anti-MHC protein antibodies; and/or (2) magnetic capture beads.

4. The kit of claim 1, further comprising a reference peptide, wherein the reference peptide is YLLEFTPPV (SEQ ID NO: 5) for HLA-A*02:01, or SIYRYYGL (SEQ ID NO: 59) for H-2Kb.

5. The kit of claim 1, further comprising a peptide exchange factor, wherein the peptide exchange factor is GM (glycine-methionine) dipeptide.

* * * * *

SEQUENCE LISTING

<160> NUMBER OF SEQ ID NOS: 68

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (4)..(4)
<223> OTHER INFORMATION: Lys(DNP)

<400> SEQUENCE: 1

```
Met Thr Tyr Lys Phe Pro Val Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys(DNP)

<400> SEQUENCE: 2

Tyr Thr Val Lys Phe Ala Leu Val
1               5

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Lys(DNP)

<400> SEQUENCE: 3

Ile Leu Lys Glu Lys Lys Val His Gly Val
1               5                   10

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(DNP)

<400> SEQUENCE: 4

Ile Leu Lys Glu Lys Val His Gly Val
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Leu Leu Glu Phe Thr Pro Pro Val
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                                peptide

<400> SEQUENCE: 6

Gln Tyr Asp Pro Val Ala Ala Leu Phe
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(DNP)

<400> SEQUENCE: 7

Ser Ile Ile Asn Lys Glu Lys Leu
1               5

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ile Leu Lys Glu Lys Lys Val His Gly Val
1               5                   10

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Ile Asn Lys Glu Lys Leu
1               5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Thr Tyr Lys Phe Pro Val Thr
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Thr Val Lys Phe Ala Leu Val
```

```
1               5
```

```
<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Leu Ala Gly Ile Gly Ile Leu Thr Val
1               5                   10

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Leu Lys Glu Pro Val His Gly Val
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Gly Ile Gly Ile Leu Thr Val
1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Ala Phe Ser Pro Glu Val Ile Pro Met Phe
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Lys(DNP)

<400> SEQUENCE: 16

Thr Phe Gln Arg Lys Pro Ala Ala Phe
1               5

<210> SEQ ID NO 17
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ile Leu Lys Glu Lys Val His Gly Val
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Met Ala Pro Arg Thr Leu Leu Leu
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Thr Asp Ala Leu Met Thr Gly Tyr
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Val Asp Pro Ile Gly His Leu Tyr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Leu Ser Glu Leu Thr Gln Gln Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Phe Met Tyr Ser Asp Phe His Phe Ile
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Leu Ala Asp Gln Leu Ile His Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Leu Ala Val Val Thr His Gly Leu
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Tyr Ser Leu Lys Leu Ser Lys Leu
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Met Asp Gln Val Pro Phe Ser Val
1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ile Tyr Ser Thr Val Ala Ser Ser Leu
1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 28

Leu Asn Met Ala Asp Lys Lys Glu Thr
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala His Tyr Asn Ile Val Thr Phe
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Val Arg Ala Tyr Thr Tyr Ser Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Tyr Met Arg Trp Thr Tyr Arg Phe
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ser Leu Tyr Asn Thr Val Ala Thr Leu
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Phe Leu Tyr Asp Asp Asn Gln Arg Val
1               5

<210> SEQ ID NO 34
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Val Leu Asp Gly Leu Leu Ser Leu
1               5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Met His Lys Val Pro Ala Ser Leu
1               5

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Cys Ile Asn Gly Val Cys Trp Thr Val
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Met His His Asn Met Asp Leu Ile
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Leu Pro Pro Pro Gly Thr Arg Val
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39
```

Leu Thr Leu Gly Glu Phe Leu Lys Leu
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ile Met Gln Leu Met Pro Phe Gly Cys
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ile Met Gln Ile Met Pro Tyr Gly Cys
1               5

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ile Lys Asp Phe Leu Arg Asn Leu
1               5

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Leu Leu Ala Val Gly Ala Thr Lys
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Ser Leu Trp Asn Gly Pro His Leu
1               5

<210> SEQ ID NO 45
<211> LENGTH: 9
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 45

Glu Tyr Ile Leu Ser Leu Glu Glu Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Leu Ala Leu Glu Val Gly Glu Leu
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Tyr Val Pro Ser Ala Glu Gln Ile
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Thr Val Gln Gly Gln Asn Leu Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ile Arg Leu Arg Pro Gly Gly Lys Lys
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ser Ile Ile Asn Phe Glu Lys Leu
1               5
```

```
<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ile Ser His Asn Phe Cys Asn Leu
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Leu Thr Phe Asn Tyr Arg Asn Leu
1               5

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Phe Ser Pro Ala Phe Asp Asn Leu
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Cys Gln Ile Phe Ala Asn Ile
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Cys Arg Pro Arg Phe Arg Glu Leu
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56
```

```
Pro Gly Cys Ala Phe Leu Thr Val
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Met Phe Asn Ala Pro Tyr Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Arg Met Tyr Ser Tyr Val Ala Thr Leu
1               5

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Ile Tyr Arg Tyr Tyr Gly Leu
1               5

<210> SEQ ID NO 60
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys(DNP)

<400> SEQUENCE: 60

Lys Leu Pro Lys Pro Pro Lys Pro Val Ser Lys Met Arg Met Ala Thr
1               5                   10                  15

Pro Leu Leu Met Gln Ala Leu Pro Met
            20                  25

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Phe Thr Glu Leu Thr Leu Gly Glu Phe
```

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Leu Met Leu Gly Glu Phe Leu Lys Leu
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ile Ser Thr Phe Lys Asn Trp Pro Lys
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ser Thr Phe Lys Asn Trp Pro Phe Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Pro Pro Ala Trp Gln Pro Phe Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Tyr Met Leu Asp Leu Gln Pro Glu Thr
1               5

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic

```
                        peptide

<400> SEQUENCE: 67

Tyr Met Leu Asp Leu Gln Pro Glu Thr Thr
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ala Gln Tyr Ile Lys Ala Asn Ser Lys Phe Ile Gly Ile Thr Glu Leu
1               5                   10                  15
```